(12) United States Patent
Pier et al.

(10) Patent No.: US 12,397,014 B2
(45) Date of Patent: Aug. 26, 2025

(54) POLYSACCHARIDE COMPOSITIONS FOR USE IN TREATING FILARIASIS

(71) Applicant: The Brigham and Women's Hospital, Inc., Boston, MA (US)

(72) Inventors: Gerald B. Pier, Brookline, MA (US); Colette Cywes Bentley, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 839 days.

(21) Appl. No.: 17/427,763

(22) PCT Filed: Feb. 5, 2020

(86) PCT No.: PCT/US2020/016863
§ 371 (c)(1),
(2) Date: Aug. 2, 2021

(87) PCT Pub. No.: WO2020/163512
PCT Pub. Date: Aug. 13, 2020

(65) Prior Publication Data
US 2022/0117997 A1    Apr. 21, 2022

Related U.S. Application Data

(60) Provisional application No. 62/801,399, filed on Feb. 5, 2019.

(51) Int. Cl.
*A61K 31/715*  (2006.01)
*A61K 47/64*  (2017.01)
*A61P 31/00*  (2006.01)
*C07K 16/18*  (2006.01)

(52) U.S. Cl.
CPC ........ *A61K 31/715* (2013.01); *A61K 47/6415* (2017.08); *A61P 31/00* (2018.01); *C07K 16/18* (2013.01); *C07K 2317/73* (2013.01)

(58) Field of Classification Search
CPC ................ A61K 31/715; A61K 47/646; A61K 47/6415; C07K 16/18; A01P 5/00; A01N 43/16
USPC ........................................................ 514/54
See application file for complete search history.

(56) References Cited

U.S. PATENT DOCUMENTS

| | | |
|---|---|---|
| 2,842,049 A | 7/1958 | Delangre |
| 4,197,290 A | 4/1980 | Yoshida |
| 4,285,936 A | 8/1981 | Pier et al. |
| 4,379,145 A | 4/1983 | Masuho et al. |
| 4,443,549 A | 4/1984 | Sadowski |
| 4,465,776 A | 8/1984 | Cidlowski et al. |
| 4,578,458 A | 3/1986 | Pier |
| 4,652,448 A | 3/1987 | Sadowski |
| 4,755,381 A | 7/1988 | Cryz |
| 4,786,592 A | 11/1988 | Deal et al. |
| 4,789,735 A | 12/1988 | Frank et al. |
| 4,795,803 A | 1/1989 | Lindberg et al. |
| 4,830,852 A | 5/1989 | Marburg et al. |
| 4,859,449 A | 8/1989 | Mattes |
| 4,879,272 A | 11/1989 | Shimoda et al. |
| 4,902,616 A | 2/1990 | Fournier et al. |
| 5,055,455 A | 10/1991 | Pier |
| 5,352,670 A | 10/1994 | Venot et al. |
| 5,362,754 A | 11/1994 | Raad et al. |
| 5,366,505 A | 11/1994 | Farber |
| 5,425,946 A | 6/1995 | Tai et al. |
| 5,571,511 A | 11/1996 | Fischer |
| 5,589,591 A | 12/1996 | Lewis |
| 5,688,516 A | 11/1997 | Raad et al. |
| 5,718,694 A | 2/1998 | Rupp |
| 5,763,191 A | 6/1998 | Knoll et al. |
| 5,830,539 A | 11/1998 | Yan et al. |
| 5,844,093 A | 12/1998 | Kettleborough et al. |
| 5,858,350 A | 1/1999 | Vournakis et al. |
| 5,866,140 A | 2/1999 | Fattom et al. |
| 5,872,215 A | 2/1999 | Osbourne et al. |
| 5,980,910 A | 11/1999 | Pier |
| 5,989,542 A | 11/1999 | Pier et al. |
| 6,235,883 B1 | 5/2001 | Jakobovits et al. |
| 6,245,735 B1 | 6/2001 | Pier |
| 6,399,066 B1 | 6/2002 | Pier |
| 6,743,431 B2 | 6/2004 | Pier |
| 6,822,072 B1 | 11/2004 | Edwards et al. |
| 6,903,194 B1 | 6/2005 | Sato et al. |
| 6,924,360 B2 | 8/2005 | Green et al. |
| 7,015,007 B2 | 3/2006 | Pier et al. |

(Continued)

FOREIGN PATENT DOCUMENTS

| | | |
|---|---|---|
| CA | 2480052 A1 | 10/2003 |
| CA | 2475736 A1 | 1/2006 |

(Continued)

OTHER PUBLICATIONS

Butt et al., *Mycobacterium smegmatis* bacteremia in an immunocompetent host. IDCases. Mar. 12, 2019:15:e00523. doi: 10.1016/j.ider.2019.e00523. eCollection 2019.

Pier, Excerpt from Chapter 2: Molecular Mechanisms of Microbial Pathogenesis. Harrison's Infectious Diseases. Eds. Dennis L. Kasper and Anthony S. Fauci. McGraw-Hill Companies, Inc. New York. 2010:9-12.

Sevrin et al., Disseminated *Mycobacterium smegmatis* Infection Associated with an Implantable Cardioverter Defibrillator. Infect. Dis. Practice. 2009;17:349-51.

Tang et al., The Relationship Between Staphylococcal Biofilm Formation Mechanism and ica locus. Microbiology China. 2008;35(8):1287-91.

(Continued)

*Primary Examiner* — Ganapathy Krishnan
(74) *Attorney, Agent, or Firm* — Wolf, Greenfield & Sacks, P.C.

(57) ABSTRACT

The disclosure relates, in part, to the use of compositions of poly N-acetylated glucosamine (PNAG), deacetylated PNAG (dPNAG), and antibodies and antibody fragments specific to PNAG in the prevention and treatment of filariasis.

15 Claims, 9 Drawing Sheets

Specification includes a Sequence Listing.

(56) References Cited

U.S. PATENT DOCUMENTS

| | | |
|---|---|---|
| 7,157,443 B2 | 1/2007 | Joyce et al. |
| 7,252,828 B2 | 8/2007 | Pier et al. |
| 7,550,569 B2 | 6/2009 | Baker et al. |
| 7,723,087 B2 | 5/2010 | Pier et al. |
| 7,786,255 B2 | 8/2010 | Pier et al. |
| 8,084,595 B2 | 12/2011 | Pier et al. |
| 8,252,894 B2 | 8/2012 | Pier et al. |
| 8,350,017 B2 | 1/2013 | Pier et al. |
| 8,410,249 B2 | 4/2013 | Pier et al. |
| 8,435,515 B2 | 5/2013 | Pier et al. |
| 8,454,979 B2 | 6/2013 | Mitarai et al. |
| 8,461,319 B2 | 6/2013 | Pier et al. |
| 8,492,364 B2 | 7/2013 | Pier et al. |
| 8,658,775 B2 | 2/2014 | Baker et al. |
| 8,663,654 B2 | 3/2014 | Pier et al. |
| 8,703,148 B2 | 4/2014 | Biemans et al. |
| 8,912,314 B2 | 12/2014 | Pier et al. |
| 8,933,218 B2 | 1/2015 | Biemans et al. |
| 9,458,227 B2 | 10/2016 | Pier et al. |
| 9,474,806 B2 * | 10/2016 | Pier ........................ A61K 39/085 |
| 10,017,563 B2 | 7/2018 | Pier et al. |
| 10,034,927 B2 * | 7/2018 | Pier .......................... A61P 31/04 |
| 10,906,962 B2 | 2/2021 | Pier et al. |
| 10,919,956 B2 | 2/2021 | Pier et al. |
| 11,123,416 B2 | 9/2021 | Pier et al. |
| 2001/0048929 A1 | 12/2001 | Chong et al. |
| 2002/0031528 A1 | 3/2002 | Fattom |
| 2002/0119166 A1 | 8/2002 | Pier et al. |
| 2003/0003100 A1 | 1/2003 | Levy et al. |
| 2003/0031528 A1 | 2/2003 | Kram |
| 2003/0113350 A1 | 6/2003 | Fattom et al. |
| 2003/0124631 A1 | 7/2003 | Pier et al. |
| 2004/0005632 A1 | 1/2004 | Erlanson et al. |
| 2004/0018198 A1 | 1/2004 | Gudas et al. |
| 2004/0091494 A1 | 5/2004 | Pier et al. |
| 2004/0175731 A1 | 9/2004 | Pier et al. |
| 2005/0025775 A1 | 2/2005 | Pier et al. |
| 2005/0118198 A1 | 6/2005 | Pier et al. |
| 2006/0115486 A1 | 6/2006 | Pier et al. |
| 2009/0162341 A1 | 6/2009 | Foster et al. |
| 2010/0021503 A1 | 1/2010 | Denoel et al. |
| 2010/0303852 A1 | 12/2010 | Biemans et al. |
| 2010/0322959 A1 | 12/2010 | Biemans et al. |
| 2011/0008385 A1 | 1/2011 | Castado et al. |
| 2011/0150880 A1 | 6/2011 | Pier et al. |
| 2012/0189700 A1 | 7/2012 | Aguilar et al. |
| 2013/0243806 A1 | 9/2013 | Pier et al. |
| 2014/0037633 A1 | 2/2014 | Pier et al. |
| 2014/0206016 A1 | 7/2014 | Sanchez et al. |
| 2015/0165016 A1 | 6/2015 | Pier et al. |
| 2015/0329620 A1 | 11/2015 | Pier et al. |
| 2016/0375117 A1 | 12/2016 | Pier et al. |
| 2017/0226194 A1 | 8/2017 | Pier et al. |
| 2018/0043023 A1 * | 2/2018 | Ilyinskii ................. A61K 39/39 |
| 2019/0117754 A1 | 4/2019 | Pier et al. |
| 2019/0127448 A1 | 5/2019 | Pier et al. |
| 2021/0363228 A1 | 11/2021 | Pier et al. |
| 2022/0175904 A1 | 6/2022 | Pier et al. |
| 2023/0382980 A1 | 11/2023 | Pier et al. |
| 2024/0358811 A1 | 10/2024 | Pier et al. |

FOREIGN PATENT DOCUMENTS

| | | |
|---|---|---|
| CN | 1252807 | 5/2000 |
| CN | 1344722 A | 4/2002 |
| CN | 101001874 A | 7/2007 |
| CN | 100351260 C | 11/2007 |
| DE | 69113102 T2 | 3/1996 |
| EP | 0 302 781 A1 | 2/1989 |
| EP | 0 574 000 A1 | 12/1993 |
| EP | 0 694 309 A2 | 10/1996 |
| EP | 2 315 747 A2 | 5/2011 |
| FR | 2 410 043 A1 | 6/1979 |
| FR | 2 581 877 A1 | 11/1986 |
| FR | 2 640 628 A1 | 6/1990 |
| GB | 2 009 771 A | 6/1979 |
| JP | H02-22234 | 1/1990 |
| JP | H11-509861 A | 8/1999 |
| JP | H11-322793 A | 11/1999 |
| JP | 2001-500528 A | 1/2001 |
| JP | 2002-503705 A | 2/2002 |
| JP | 2002-520374 A | 7/2002 |
| JP | 2005-515237 A | 5/2005 |
| JP | 2006-513166 A | 4/2006 |
| JP | 2008-501317 A | 1/2008 |
| KR | 10-2005-0074582 A | 7/2005 |
| WO | WO 85/05037 A1 | 11/1985 |
| WO | WO 86/02358 A1 | 4/1986 |
| WO | WO 88/02028 A1 | 3/1988 |
| WO | WO 89/04873 A1 | 6/1989 |
| WO | WO 90/03398 A1 | 4/1990 |
| WO | WO 90/06696 A2 | 6/1990 |
| WO | WO 93/01276 A1 | 1/1993 |
| WO | WO 93/09811 A1 | 5/1993 |
| WO | WO 93/19373 A1 | 9/1993 |
| WO | WO 94/15640 A1 | 7/1994 |
| WO | WO 97/17334 A1 | 5/1997 |
| WO | WO 97/19105 A1 | 5/1997 |
| WO | WO 98/47915 A1 | 10/1998 |
| WO | WO 98/52605 A1 | 11/1998 |
| WO | WO 99/40440 A1 | 8/1999 |
| WO | WO 99/42130 A1 | 8/1999 |
| WO | WO 00/03745 A2 | 1/2000 |
| WO | WO 00/35504 A1 | 6/2000 |
| WO | WO 00/56360 A2 | 9/2000 |
| WO | WO 01/41800 A2 | 6/2001 |
| WO | WO 2002/094983 A2 | 11/2002 |
| WO | WO 2003/053462 A2 | 7/2003 |
| WO | WO 2003/061558 A2 | 7/2003 |
| WO | WO 2003/080672 A1 | 10/2003 |
| WO | WO 2003/085093 A2 | 10/2003 |
| WO | WO 2003/087054 A2 | 10/2003 |
| WO | WO 2004/043405 A2 | 5/2004 |
| WO | WO 2004/043407 A2 | 5/2004 |
| WO | WO 2004/080490 A2 | 9/2004 |
| WO | WO 2005/000346 A1 | 1/2005 |
| WO | WO 2005/016973 A1 | 2/2005 |
| WO | WO 2005/103084 A2 | 11/2005 |
| WO | WO 2006/032472 A2 | 3/2006 |
| WO | WO 2006/065503 A2 | 6/2006 |
| WO | WO 2006/065553 A2 | 6/2006 |
| WO | WO 2006/096970 A1 | 9/2006 |
| WO | WO 2006/100108 A1 | 9/2006 |
| WO | WO 2007/113223 A2 | 10/2007 |
| WO | WO 2007/113224 A2 | 10/2007 |
| WO | WO2010/011284 A2 * | 1/2010 ........... A61K 31/085 |
| WO | WO 2013/181348 A1 | 12/2013 |

OTHER PUBLICATIONS

U.S. Appl. No. 10/713,790, filed Nov. 12, 2003, Granted, U.S. Pat. No. 10,919,956.

U.S. Appl. No. 10/712,391, filed Nov. 12, 2003, Granted, U.S. Pat. No. 7,723,087.

U.S. Appl. No. 11/111,688, filed Apr. 21, 2005, Granted, U.S. Pat. No. 7,786,255.

U.S. Appl. No. 12/824,510, filed Jun. 28, 2010, Granted, U.S. Pat. No. 8,084,595.

U.S. Appl. No. 13/103,532, filed May 9, 2011, Granted, U.S. Pat. No. 8,252,894.

U.S. Appl. No. 14/548,173, filed Nov. 19, 2014, Granted, U.S. Pat. No. 9,458,227.

U.S. Appl. No. 16/005,647, filed Jun. 11, 2018, Granted, U.S. Pat. No. 10,906,962.

U.S. Appl. No. 17/131,613, filed Dec. 22, 2020, Published, 2021-0363228.

U.S. Appl. No. 13/055,178, filed Mar. 2, 2011, Granted, U.S. Pat. No. 8,492,364.

U.S. Appl. No. 13/924,435, filed Jun. 21, 2013, Granted, U.S. Pat. No. 9,474,806.

U.S. Appl. No. 15/258,417, filed Sep. 7, 2016, Granted, U.S. Pat. No. 10,034,927.

(56) References Cited

OTHER PUBLICATIONS

U.S. Appl. No. 16/016,473, filed Jun. 22, 2018, Granted, U.S. Pat. No. 11,123,416.
U.S. Appl. No. 17/408,287, filed Aug. 20, 2021, Pending.
U.S. Appl. No. 14/404,303, filed Nov. 26, 2014, Published, 2015-0165016.
U.S. Appl. No. 12/294,689, filed Sep. 26, 2008, Granted, U.S. Pat. No. 8,703,148.
U.S. Appl. No. 12/294,643, filed Sep. 26, 2008, Granted, U.S. Pat. No. 8,933,218.
PCT/US2020/016863, May 7, 2020, International Search Report and Written Opinion.
PCT/US2020/016863, Aug. 19, 2021, International Preliminary Report on Patentability.
International Search Report and Written Opinion mailed May 7, 2020 for Application No. PCT/US2020/016863.
International Preliminary Report on Patentability mailed Aug. 19, 2021 for Application No. PCT/US2020/016863.
[No Author Listed] ATCC Catalogue website 2001; ATCC No. 35984.
[No Author Listed] ATCC Catalogue: Bacteria and Bacteriophages; 1992; 18$^{th}$ Edition; p. 301.
[No. Author Listed] Five Surprising Facts about Pneumococcal Pneumonia. American Lung Association. Nov. 2017. Available at http://www.lung.org/about-us/media/top-stories/five-surprising-facts-about-pneumococcal-pneumonia.html. Last accessed Mar. 8, 2018. Pages 1-3.
[No Author Listed] Pneumococcal Disease, Transmission and Those at High Risk. CDC Control and Prevention Sep. 2017. Available at http://www.cdc.gov/pneumococcal/about/risk-transmission.html. Last accessed Mar. 8, 2018. pp. 1-2.
No Author Listed, The New Riverside University Dictionary, The Riverside Publishing Company, p. 933, 1984.
No Author Listed, Illustrated Stedman's Medical Dictionary, 24$^{th}$ edition, Williams and Wilkins, London, p. 707, 1982.
No Author Listed, New York Times Editorial, Another Very Scary Germ. Nov. 20, 2007. Available at http://www.nytimes.com/2007/11/20/opinion/20tue2.html_r=2&oref=slogin&pagewanted. Last accessed Apr. 30, 2010. 2 pages.
[No Author Listed] Adis R&D Profile Drug in R&D. Adis International. 2003;4(6):383-5. Available at http://www.ingentaconnect.com/content/adis/rdd//2003/00000004/00000006/art00013. Last accessed Nov. 11, 2010. Abstract only.
GenBank Submission; NIH/BCBI; Accession No. AAZ87998; Pier et al; May 31, 2000.
GenBank Submission; NIH/NCBI, Accession No. BA000018; Kuroda et al.; Oct. 22, 2004 (last submission).
GenBank Submission; NIH/NCBI Accession No. AF086783. Oct. 1, 1999. Cramton et al.
GenBank Submission; NIH/NCBI, Accession No. DQ231549; Kelly-Quintos et al.; Printed May 9, 2006.
GenBank Submission; NIH/NCBI, Accession No. DQ231550; Kelly-Quintos et al.; Printed May 9, 2006.
GenBank Submission; NIH/NCBI, Accession No. DQ231551; Kelly-Quintos et al.; Printed May 9, 2006.
GenBank Submission; NIH/NCBI, Accession No. DQ231552; Kelly-Quintos et al.; Printed May 9, 2006.
GenBank Submission; NIH/NCBI, Accession No. DQ231553; Kelly-Quintos et al.; Printed May 9, 2006.
GenBank Submission; NIH/NCBI, Accession No. DQ231554; Kelly-Quintos et al.; Printed May 9, 2006.
EBI DBfetch submission; EMBL-EBI; Accession No. U43366; Heilmann et al, Apr. 17, 2005 (last submission).
Allignet et al., Tracking adhesion factors in *Staphylococcus caprae* strains responsible for human bone infections following implantation of orthopaedic material. Microbiology. Aug. 1999; 145 (Pt 8):2033-42.
Ammendolia et al., Slime production and expression of the slime-associated antigen by staphylococcal clinical isolates. J Clin Microbiol. Oct. 1999;37(10):3235-8.

Arciola et al., In catheter infections by *Staphylococcus epidermidis* the intercellular adhesion (ica) locus is a molecular marker of the virulent slime-producing strains. J Biomed Mater Res. Mar. 5, 2002;59(3):557-62. Abstract Only.
Baldassarri et al., Purification and characterization of the staphylococcal slime-associated antigen and its occurrence among *Staphylococcus epidermis* clinical isolates. Infect Immun. Aug. 1996;64(8):3410-5.
Barsham et al., Detection of antibodies to *Staphylococcus epidermidis* in infected total hip replacements by an enzyme linked immunosorbent assay. J Clin Pathol. Jul. 1985;38(7):839-40.
Bernstein, et al., Antibody coated bacteria in otitis media with effusions. Ann Otol Rhinol Laryngol Suppl. May-Jun. 1980;89(3 Pt 2): 104-9. Abstract only.
Bhasin et al., Identification of a gene essential for O-acetylation of the *Staphylococcus aureus* type 5 capsular polysaccharide. Mol Microbiol. Jan. 1998;27(1):9-21. Abstract Only.
Bobrov et al., Insights into Yersinia pestis biofilm development: topology and co-interaction of Hms inner membrane proteins involved in exopolysaccharide production. Environ Microbiol. Jun. 2008;10(6):1419-32. doi: 10.1111/j.1462-2920.2007.01554.x.
Brown et al., Tolerance to single, but not multiple, amino acid replacements in antibody V-H CDR2: A means of minimizing B cell wastage from somatic hypermutation? J Immunol. Jan. 1, 1996;156(9): 3285-3291.
Burgeot et al., Immunopotentiation of *Staphylococcus aureus* type 5 capsular polysaccharide co-entrapped in liposomes with alpha-toxin. Vaccine. Feb. 28, 2001;19(15-16):2092-9. Abstract only.
Capek et al., Chapters 22: Carbohydrates and Chapter 23: Polysaccharides. In: Journal of Chromatography Journal Library, vol. 3: Liquid column Chromatography, A Survey of Modern Technicques and Applications. Deyl et al., eds. Elsevier Scientific Publishing Company: New York, 1975:465-528.
Cerca et al., Comparative antibody-mediated phagocytosis of *Staphylococcus epidermidis* cells grown in a biofilm or in the planktonic state. Infect Immun. Aug. 2006;74(8):4849-55.
Cerca et al., Influence of batch or fed-batch growth on Staphylococcus epidermidis biofilm formation. Lett Appl Microbiol. 2004;39(5):420-4.
Cerca et al., Molecular basis for preferential protective efficacy of antibodies directed to the poorly acetylated form of staphylococcal poly-N-acetyl-beta-(1-6)-glucosamine. Infect Immun. Jul. 2007;75(7):3406-13. Epub Apr. 30, 2007.
Cerca et al., Protection against *Escherichia coli* infection by antibody to the *Staphylococcus aureus* poly-N-acetylglucosamine surface polysaccharide. Proc Natl Acad Sci U S A. May 1, 2007;104(18):7528-33. Epub Apr. 19, 2007.
Chanter, Partial purification and characterization of two non K99 mannose-resistant haemagglutinins of *Escherichia coli* B41. J Gen Microbiol. Jan. 1983;129(1):235-43.
Chen et al., Characterization and biological properties of chemically deglycosylated human chorionic gonadotropin. Role of carbohydrate moieties in adenylate cyclase activation. J Biol Chem. Dec. 10, 1982;257(23):14446-52.
Chiavolini et al., Animal models of *Streptococcus pneumoniae* disease. Clin Microbiol Rev. Oct. 2008;21(4):666-85. doi: 10.1128/CMR.00012-08.
Chibba et al., Synthesis and evaluation of inhibitors of *E. coli* PgaB, a polysaccharide de-N-acetylase involved in biofilm formation. Org Biomol Chem. Sep. 21, 2012;10(35):7103-7. doi:10.1039/c2ob26105g. Epub Aug. 2, 2012.
Christensen et al., Adherence of slime-producing strains of *Staphylococcus epidermidis* to smooth surfaces. Infect Immun. Jul. 1982;37(1):318-26.
Chu et al., Preparation, characterization, and immunogenicity of conjugates composed of the O-specific polysaccharide of Shigella dysenteriae type 1 (Shiga's bacillus) bound to tetanus toxoid. Infect Immun. Dec. 1991;59(12):4450-8.
Conlon et al., icaR encodes a transcriptional repressor involved in environmental regulation of ica operon expression and biofilm formation in *Staphylococcus epidermidis*. J Bacteriol. Aug. 2002; 184(16):4400-8.

(56) References Cited

OTHER PUBLICATIONS

Conlon et al., Regulation of icaR gene expression in *Staphylococcus epidermidis*. FEMS Microbiol Lett. Nov. 5, 2002;216(2):171-7.
Conover et al., The Bps polysaccharide of Bordetella pertussis promotes colonization and biofilm formation in the nose by functioning as an adhesin. Mol Microbiol. Sep. 2010;77(6):1439-55. doi: 10.1111/j.1365-2958.2010.07297.x.
Cramton et al., Anaerobic conditions induce expression of polysaccharide intercellular adhesin in *Staphylococcus aureus* and *Staphylococcus epidermidis*. Infect Immun. Jun. 2001;69(6):4079-85.
Cramton et al., The intercellular adhesion (ica) locus is present in *Staphylococcus aureus* and is required for biofilm formation. Infect Immun. Oct. 1999;67(10):5427-33.
Cywes-Bentley et al., Antibody to a conserved antigenic target is protective against diverse prokaryotic and eukaryotic pathogens. Proc Natl Acad Sci U S A. Jun. 11, 2013;110(24):E2209-18. doi: 10.1073/pnas.1303573110. Epub May 28, 2013.
Cywes-Bentley et al., Supporting Information for Antibody to a conserved antigenic target is protective against diverse prokaryotic and eukaryotic pathogens. Proc Natl Acad Sci U S A. Jun. 11, 2013;110(24):E2209-18. doi: 10.1073/pnas.1303573110. Epub May 28, 2013.
De Velasco et al., Anti-polysaccharide immunoglobulin isotype levels and opsonic activity of antisera: relationships with protection against *Streptococcus pneumoniae* infection in mice. J Infect Dis. Aug. 1995;172(2):562-5. doi: 10.1093/infdis/172.2.562.
Depascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Dobinsky et al., Influence of Tn917 insertion on transcription of the icaADBC operon in six biofilm-negative transposon mutants of *Staphylococcus epidermidis*. Plasmid. Jan. 2002;47(1):10-7. Abstract Only.
Dobrin, et al., The role of complement, immunoglobulin and bacterial antigen in coagulase-negative staphylococcal shunt nephritis. Am J Med. Nov. 1975;59(5):660-73. Abstract only.
Elder et al., Characterization of monoclonal antibodies specific for adhesion: isolation of an adhesin of *Streptococcus sanguis* FW213. Infect Immun. Nov. 1986;54(2):421-7.
Espersen, et al., Enzyme-linked immunosorbent assay for detection of *Staphylococcus epidermidis* antibody in experimental *S. epidermidis* endocarditis. J Clin Microbiol. Feb. 1986;23(2):339-42.
Espersen, et al., Solid-phase radioimmunoassay for IgG antibodies to *Staphylococcus epidermidis*. Use in serious coagulase-negative staphylococcal infections. Arch Intern Med. Apr. 1987;147(4):689-93. Abstract only.
Fattom et al., Antigenic determinants of *Staphylococcus aureus* type 5 and type 8 capsular polysaccharide vaccines. Infect Immun. Oct. 1998;66(10):4588-92.
Fattom et al., Comparative immunogenicity of conjugates composed of the *Staphylococcus aureus* type 8 capsular polysaccharide bound to carrier proteins by adipic acid dihydrazide or N-succinimidyl-3-(2-pyridyldithio)propionate. Infect Immun. Feb. 1992;60(2):584-9.
Fattom et al., Development of StaphVAX, a polysaccharide conjugate vaccine against *S. aureus* infection: from the lab bench to phase III clinical trials. Vaccine. Feb. 17, 2004;22(7):880-7. Abstract only.
Fattom et al., Effect of conjugation methodology, carrier protein, and adjuvants on the immune response to *Staphylococcus aureus* capsular polysaccharides. Vaccine. Oct. 1995;13(14):1288-93.
Fattom et al., Synthesis and immunologic properties in mice of vaccines composed of *Staphylococcus aureus* type 5 and type 8 capsular polysaccharides conjugated to Pseudomonas aeruginosa exotoxin A. Infect Immun. Jul. 1990;58(7):2367-74.
Ferreiros et al., Purification and partial characterization of a K99-antigen associated adhesin in *Escherichia coli* (637 strain). Rev Esp Fisiol. Mar. 1983;39(1):45-50.

Fey et al., Characterization of the relationship between polysaccharide intercellular adhesin and hemagglutination in *Staphylococcus epidermidis*. J Infect Dis. Jun. 1999;179(6):1561-4. Abstract Only.
Fitzpatrick et al., Environmental regulation of biofilm formation in intensive care unit isolates of *Staphylococcus epidermidis*. J Hosp Infect. Nov. 2002;52(3):212-8.
Fournier et al., Purification and characterization of *Staphylococcus aureus* type 8 capsular polysaccharide. Infect Immun. Jul. 1984;45(1):87-93.
Fowler et al., The intercellular adhesin locus ica is present in clinical isolates of *Staphylococcus aureus* from bacteremic patients with infected and uninfected prosthetic joints. Med Microbiol Immunol (Berl). Apr. 2001;189(3):127-31. Abstract Only.
Frebourg et al., PCR-Based assay for discrimination between invasive and contaminating *Staphylococcus epidermidis* strains. J Clin Microbiol. Feb. 2000;38(2):877-80.
Fridman et al., One-pot synthesis of glucosamine oligosaccharides. Org Lett. Jan. 24, 2002;4(2):281-3.
Gehron et al., Determination of the gram-positive bacterial content of soils and sediments by analysis of teichoic acid components. J Microbiol Methods. 1984;2:165-76.
Gelosia et al., Phenotypic and genotypic markers of *Staphylococcus epidermidis* virulence. Clin Microbiol Infect. Apr. 2001;7(4):193-9. Abstract Only.
Gening et al., Synthesis of beta-(1-->6)-linked glucosamine oligosaccharides corresponding to fragments of the bacterial surface polysaccharide poly-N-acetylglucosamine. Carbohydr Res. Feb. 26, 2007;342(3-4):567-75. Epub Sep. 6, 2006.
Gening et al., Synthetic {beta}-(1->6)-linked N-acetylated and nonacetylated oligoglucosamines used to produce conjugate vaccines for bacterial pathogens. Infect Immun. Feb. 2010;78(2):764-72. Epub Nov. 30, 2009.
Gening et al., The study of the reaction of terminated oligomerization in the synthesis of oligo-(beta1-6)-glucosamines. Bioorg Khim. Jul.-Aug. 2006;32(4):432-43. Published in English in Russian Journal of Biorganic Chemistry, 2006;32(4):389-99.
Gerke et al., Characterization of the N-acetylglucosaminyltransferase activity involved in the biosynthesis of the *Staphylococcus epidermidis* polysaccharide intercellular adhesin. J Biol Chem. Jul. 17, 1998;273(29):18586-93.
Gerke et al., Experimental Pseudomonas aeruginosa Infection of the Mouse Cornea. Infect Immun. Feb. 1971;3(2):209-16.
Götz, *Staphylococcus and biofilms*. Mol Microbiol. Mar. 2002;43(6):1367-78.
Grachev et al., NMR and conformational studies of linear and cyclic oligo-(1 →6)-β-D-glucosamines. Carbohydr Res. Nov. 8, 2011;346(15):2499-510. Epub Sep. 5, 2011.
Gray et al., Effect of extracellular slime substance from *Staphylococcus epidermidis* on the human cellular immune response. Lancet. Feb. 18, 1984;1(8373):365-7.
Heilmann et al., Characterization of Tn917 insertion mutants of *Staphylococcus epidermidis* affected in biofilm formation. Infect Immun. Jan. 1996;64(1):277-82.
Heilmann et al., Further characterization of *Staphylococcus epidermidis* transposon mutants deficient in primary attachment or intercellular adhesion. Zentralbl Bakteriol. Jan. 1998;287(1-2):69-83. Abstract Only.
Heilmann et al., Molecular basis of intercellular adhesion in the biofilm-forming *Staphylococcus epidermidis*. Mol Microbiol. Jun. 1996;20(5):1083-91.
Hermanson, Bioconjugate Techniques. Academic Press. 1996:34, 187-248.
Hinnebusch et al., Yersinia pestis Biofilm in the Flea Vector and Its Role in the Transmission of Plague. Curr Top Microbiol Immunol. 2008; 322: 229-48.
Hogt et al., Cell surface characteristics of coagulase-negative staphylococci and their adherence to fluorinated poly(ethylenepropylene). Infect Immun. Jan. 1986;51(1):294-301.
Huang et al., Risk of methicillin-resistant *Staphylococcus aureus* infection after previous infection or colonization. Clin Infect Dis. Feb. 1, 2003;36(3):281-5. Epub Jan. 17, 2003.

(56) References Cited

OTHER PUBLICATIONS

Ichiman et al., Induction of resistance with heat-killed unencapsulated strains of *Staphylococcus epidermidis* against challenge with encapsulated strains of *Staphylococcus epidermidis*. Microbiol Immunol. 1989;33(4):277-86.
Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;71(2):176-81.
Ichiman et al., Specificity of monoclonal antibodies against an encapsulated strain of *Staphylococcus epidermidis*. in The Staphylococci, Zbl Bakt. 1991;Suppl 21:150-2.
Ichiman et al., The relationship of capsular-type of *Staphylococcus epidermidis* to virulence and induction of resistance in the mouse. J Appl Bacteriol. Oct. 1981;51(2):229-41.
Jabbouri et al., Characteristics of the biofilm matrix and its role as a possible target for the detection and eradication of *Staphylococcus epidermidis* associated with medical implant infections. FEMS Immunol Med Microbiol. Aug. 2010;59(3):280-91. Doi: 10.1111/j.1574-695X.2010.00695.x. Epub May 12, 2010.
Jacques et al., Chemoenzymatic synthesis of GM3 and GM2 gangliosides containing a truncated ceramide functionalized for glycoconjugate synthesis and solid phase applications. Org Biomol Chem. Jan. 7, 2006;4(1):142-54. Epub Nov. 30, 2005.
Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.
Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004;186(8):2449-56.
Ji et al., Identification of critical staphylococcal genes using conditional phenotypes generated by antisense RNA. Science. Sep. 21, 2001;293(5538):2266-9.
Ji et al., Regulated antisense RNA eliminates alpha-toxin virulence in *Staphylococcus aureus* infection. J Bacteriol. Nov. 1999;181(21):6585-90.
Johnson et al., Interference with granulocyte function by *Staphylococcus epidermidis* slime. Infect Immun. Oct. 1986;54(1):13-20.
Jones, Revised structures for the capsular polysaccharides from *Staphylococcus aureus* Types 5 and 8, components of novel glycoconjugate vaccines. Carbohydr Res. May 2, 2005;340(6):1097-106. Abstract only.
Joyce et al., Isolation, structural characterization, and immunological evaluation of a high-molecular-weight exopolysaccharide from *Staphylococcus aureus*. Carbohydr Res. Apr. 22, 2003;338(9):903-22.
Kaplan et al., Genes involved in the synthesis and degradation of matrix polysaccharide in Actinobacillus actinomycetemcomitans and Actinobacillus pleuropneumoniae biofilms. J Bacteriol. Dec. 2004;186(24):8213-20.
Kelly-Quintos et al., Biological Characterization of Fully Human Monoclonal Antibodies to Staphylococcal Surface Polysaccharide PNAG. Abstracts of the 104th General Meeting of the American Society for Microbiology. Am Soc Microbiol. May 2004. Abstract A-63. Abstract and corresponding presentation.
Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.
Kelly-Quintos et al., The role of epitope specificity in the human opsonic antibody response to the staphylococcal surface polysaccharide poly N-acetyl glucosamine. J Infect Dis. Dec. 1, 2005;192(11):2012-9. Epub Nov. 1, 2005.
Keutmann et al., Evidence for a conformational change in deglycosylated glycoprotein hormones. FEBS Lett. Jun. 17, 1985;185(2):333-8.
Kille et al., Sucralose: assessment of teratogenic potential in the rat and the rabbit. Food Chem Toxicol. 2000;38 Suppl 2:S43-52.
Klevens et al., Invasive methicillin-resistant *Staphylococcus aureus* infections in the United States. JAMA. Oct. 17, 2007;298(15):1763-71.
Kohler, Derivation and diversification of monoclonal antibodies. Science. Sep. 19, 1986;233(4770):1281-6.
Kojima et al., Antibody to the capsular polysaccharide/adhesin protects rabbits against catheter-related bacteremia due to coagulase-negative staphylococci. J Infect Dis. Aug. 1990; 162(2):435-41.
Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.
Kossaczka et al., Synthesis and immunological properties of Vi and di-O-acetyl pectin protein conjugates with adipic acid dihydrazide as the linker. Infect Immun. Jun. 1997;65(6):2088-93.
Kropec et al., Poly-N-acetylglucosamine production in *Staphylococcus aureus* is essential for virulence in murine models of systemic infection. Infect Immun. Oct. 2005;73(10):6868-76.
Kuehnert et al., Methicillin-resistant-*Staphylococcus aureus* hospitalizations, United States. Emerg Infect Dis. Jun. 2005;11(6):868-72.
Kuroda et al., Whole genome sequencing of meticillin-resistant *Staphylococcus aureus*. Lancet. Apr. 21, 2001;357(9264):1225-40.
Lee et al., Chemical characterization and immunogenicity of capsular polysaccharide isolated from mucoid *Staphylococcus aureus*. Infect Immun. Sep. 1987;55(9):2191-7.
Lee et al., Effect of a trivalent vaccine against *Staphylococcus aureus* mastitis lymphocyte subpopulations, antibody production, and neutrophil phagocytosis. Can J Vet Res. Jan. 2005;69(1):11-8.
Lee et al., Protective efficacy of antibodies to the *Staphylococcus aureus* type 5 capsular polysaccharide in a modified model of endocarditis in rats. Infect Immun. Oct. 1997;65(10):4146-51.
Leith et al., Purification of a Mycoplasma pneumoniae adhesin by monoclonal antibody affinity chromatography. J Bacteriol. Feb. 1984;157(2):678-80.
Leung et al., Efficient synthesis and protein conjugation of beta-(1-->6)-D-N-acetylglucosamine oligosaccharides from the polysaccharide intercellular adhesin. Carbohydr Res. Mar. 31, 2009;344(5):570-5. Epub Jan. 3, 2009.
Locksley, Chapter 94: Staphylococcal Infections. In Harrison's Principles of Internal Medicine, Eleventh Edition. Braunwald et al., eds. McGraw-Hill Book Company, Inc.: New York, 1950. p. 537-43.
Longworth et al., O-Acetylation status of the capsular polysaccharides of serogroup Y and W135 meningococci isolated in the UK. FEMS Immunol Med Microbiol. Jan. 14, 2002;32(2):119-23. Abstract Only.
Ludwicka et al., Investigation on extracellular slime substance produced by *Staphylococcus epidermidis*. Zentralbl Bakteriol Mikrobiol Hyg [A]. Dec. 1984;258(2-3):256-67.
MacCallum et al., Antibody-antigen interactions: contact analysis and binding site topography. J Mol Biol. Oct. 11, 1996;262(5):732-45.
Mack et al., Association of biofilm production of coagulase-negative staphylococci with expression of a specific polysaccharide intercellular adhesin. J Infect Dis. Oct. 1996; 174(4):881-4.
Mack et al., Characterization of transposon mutants of biofilm-producing *Staphylococcus epidermidis* impaired in the accumulative phase of biofilm production: genetic identification of a hexosamine-containing polysaccharide intercellular adhesin. Infect Immun. Aug. 1994;62(8):3244-53.
Mack et al., Essential functional role of the polysaccharide intercellular adhesin of *Staphylococcus epidermidis* in hemagglutination. Infect Immun. Feb. 1999;67(2):1004-8.
Mack et al., Genetic and biochemical analysis of *Staphylococcus epidermidis* biofilm accumulation. Methods Enzymol. 2001;336:215-39.
Mack et al., Identification of three essential regulatory gene loci governing expression of *Staphylococcus epidermidis* polysaccharide intercellular adhesin and biofilm formation. Infect Immun. Jul. 2000;68(7):3799-807.
Mack et al., Molecular mechanisms of *Staphylococcus epidermidis* biofilm formation. J Hosp Infect. Dec. 1999;43 Suppl:S113-25. Abstract Only.

(56) References Cited

OTHER PUBLICATIONS

Mack et al., Parallel induction by glucose of adherence and a polysaccharide antigen specific for plastic-adherent *Staphylococcus epidermidis*: evidence for functional relation to intercellular adhesion. Infect Immun. May 1992;60(5):2048-57.
Mack et al., The intercellular adhesin involved in biofilm accumulation of *Staphylococcus epidermidis* is a linear beta-1,6-linked glucosaminoglycan: purification and structural analysis. J Bacteriol. Jan. 1996;178(1):175-83.
Maira-Litran et al., Biologic properties and vaccine potential of the staphylococcal poly-N-acetyl glucosamine surface polysaccharide. Vaccine. Feb. 17, 2004;22(7):872-9. Review.
Maira-Litrán et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Erratum: Infect Immun. Nov. 2005;73(11):7789.
Maira-Litran et al., Deacetylated-poly-N-acetyl Glucosamine (dPNAG) Polysaccharide Conjugated to Diphtheria Toxoid (DT) Confers Protection Against Multiple Strains of *Staphylococcus aureus* in a Murine Model of Bacteremia. Abstracts of the 104th General Meeting of the American Society for Microbiology. Am Soc Microbiol. May 2004. Abstract D-130. Abstract and corresponding presentation.
Maira-Litran et al., Immunochemical properties of the staphylococcal poly-N-acetylglucosamine surface polysaccharide. Infect Immun. Aug. 2002;70(8):4433-40.
Maira-Litran et al., Relationship Between the Polysacharide Intercellular Adhesin (PIA) and Poly-N-Succinyl b-1-6 Glucosamine (PNSG) Molecules Produced by Pathogenic Staphylococi. In: Abstracts of the General Meeting of the American Society for Microbiology. Session No. 31/D. May 2001:283-4. Abstract No. D42.
Maira-Litran et al., Synthesis and Immunological Properties of a Staphylococcal Deacetylated-poly-N-acetyl Glucosamine (dPNAG) Polysaccharide and Clumping Factor A (ClfA) Protein Conjugate Vaccine. Abstracts of the 104th General Meeting of the American Society for Microbiology. Am Soc Microbiol. May 2004. Abstract E-062. Abstract and corresponding presentation.
McKenney et al., Broadly protective vaccine for *Staphylococcus aureus* based on an in vivo-expressed antigen. Science. May 28, 1999;284(5419):1523-7.
Mckenney et al., The ica locus of *Staphylococcus epidermidis* encodes production of the capsular polysaccharide/adhesin. Infect Immun. Oct. 1998;66(10):4711-20.
Mckenney et al., Vaccine potential of poly-1-6 beta-D-N-succinylglucosamine, an immunoprotective surface polysaccharide of *Staphylococcus aureus* and *Staphylococcus epidermidis*. J Biotechnol. Sep. 29, 2000;83(1-2):37-44.
McNeely et al., Antibody responses to capsular polysaccharide backbone and O-acetate side groups of *Streptococcus pneumoniae* type 9V in humans and rhesus macaques. Infect Immun. Aug. 1998;66(8):3705-10.
Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23):1893-916.
Michon et al., Structure activity studies on group C meningococcal polysaccharide-protein conjugate vaccines: effect of O-acetylation on the nature of the protective epitope. Dev Biol (Basel). 2000;103:151-60. Abstract Only.
Mikayama et al., Molecular cloning and functional expression of a cDNA encoding glycosylation-inhibiting factor. Proc Natl Acad Sci U S A. Nov. 1, 1993;90(21):10056-60.
Milstein, From antibody structure to immunological diversification of immune response. Science. Mar. 14, 1986;231(4743):1261-8.
Moch et al., Isolation and characterization of the alpha-sialyl-beta-2,3-galactosyl-specific adhesin from fimbriated *Escherichia coli*. Proc Natl Acad Sci U S A. May 1987;84(10):3462-6.
Moreau et al., Structure of the type 5 capsular polysaccharide of *Staphylococcus aureus*. Carbohydr Res. Jul. 1, 1990;201(2):285-97.

Muller et al., Capsular polysaccharide/adhesin (PS/A) production by coagulase-negative staphylococci (CNS) is associated with adherence to silastic tubing. 1989:49. Abstract B-111.
Muller et al., Occurrence of capsular polysaccharide/adhesin among clinical isolates of coagulase-negative staphylococci. J Infect Dis. Nov. 1993;168(5):1211-8.
Nagy et al., Multi-adhesin vaccines for the protection of the neonatal piglet against "*E. coli*" infections. Dev Biol Stand. 1983;53:189-97.
Nagy et al., Recombinant Antibodies for Infectious Diseases, Advances in Experimental Medicine and Biology. Chapter 7. Springer Nature. 2017;1053:119-153. Doi: https://doi.org/10.1007/978-3-319-72077-7_7.
Nakano, et al., Polyclonal antibody production in murine spleen cells induced by *Staphylococcus*. Microbiol Immunol. 1980;24(10):981-94. Abstract only.
O'Brien et al., Production of antibodies to *Staphylococcus aureus* serotypes 5, 8, and 336 using poly(DL-lactide-co-glycolide) microspheres. J Dairy Sci. Aug. 2000;83(8):1758-66.
O'Gara et al., *Staphylococcus epidermidis* biofilms: importance and implications. J Med Microbiol. Jul. 2001;50(7):582-7.
Ohlsen et al., Immunotherapeutic strategies to combat staphylococcal infections. Int J Med Microbiol. Aug. 2010;300(6):402-10. Doi: 10.1016/j.ijmm.2010.04.015. Epub May 23, 2010.
Ohshima et al., Cell surface antigen of encapsulated *Staphylococcus epidermidis* ATCC 31432. J Clin Microbiol. Jul. 1987;25(7):1338-40.
Ohshima et al., Immunochemical characterization and biological properties of a cell surface antigen extracted from encapsulated *Staphylococcus epidermidis* strain SE-10. Zentralbl Bakteriol 1990;274:417-25.
Ohshima et al., Protection inducing antigen of an encapsulated *Staphylococcus epidermis* SE-10. in The Staphylococci, Zbl Bakt. 1991;Suppl 21:278-80.
Orskov et al., An adhesive protein capsule of *Escherichia coli*. Infect Immun. Jan. 1985;47(1):191-200.
Parise et al., Role of a putative polysaccharide locus in Bordetella biofilm development. J Bacteriol. Feb. 2007;189(3):750-60.
Pavliak, Carb 40-*Staphylococcus aureus* capsular polysaccharide—MSCRAMM protein conjugate vaccines. The $232^{nd}$ ACS National Meeting, San Francisco, CA. Sep. 10-14, 2006:40.
Peters et al., Biology of *S. epidermidis* extracellular slime. In The Staphylococci, Zbl Bakt . 1987;Suppl 16:15-33.
Peterson et al., The key role of peptidoglycan in the opsonization of *Staphylococcus aureus* . J Clin Invest. Mar. 1978;61(3):597-609.
Pier et al., Further purification and characterization of high-molecular-weight polysaccharide from Pseudomonas aeruginosa. Infect Immun. Dec. 1983;42(3):936-41.
Pier et al., Isolation and characterization of a high-molecular-weight polysaccharide from the slime of Pseudomonas aeruginosa. Infect Immun. Dec. 1978;22(3):908-18.
Pier et al., Protective immunity induced in mice by immunization with high-molecular-weight polysaccharide from Pseudomonas aeruginosa. Infect Immun. Dec. 1978;22(3):919-25.
Pollack et al., Functional properties of isotype-switched immunoglobulin M (IgM) and IgG monoclonal antibodies to Pseudomonas aeruginosa lipopolysaccharide. Infect Immun. Nov. 1995;63(11):4481-8.
Posner et al., Epstein Barr virus transformation of peripheral blood B cells secreting antibodies reactive with cell surface antigens. Autoimmunity. 1990;8(2):149-58.
Pozzi et al., Opsonic and protective properties of antibodies raised to conjugate vaccines targeting six *Staphylococcus aureus* antigens. PLoS One. 2012;7(10):e46648. doi: 10.1371/journal.pone.0046648. Epub Oct. 15, 2012.
Preston et al., Production and characterization of a set of mouse-human chimeric immunoglobulin G (IgG) subclass and IgA monoclonal antibodies with identical variable regions specific for *Pseudomonas aeruginosa* serogroup 06 lipopolysaccharide. Infect Immun. Sep. 1998;66(9):4137-42.
Preston et al., Prophylactic and therapeutic efficacy of immunoglobulin G antibodies to *Pseudomonas aeruginosa* lipopolysac-

(56) References Cited

OTHER PUBLICATIONS charide against murine experimental corneal infection. Invest Ophthalmol Vis Sci. Jun. 1997;38(7):1418-25.
Propst et al., Abstracts of the General Meeting of the American Society for Microbiology. 1998;42:242. Abstract only. 2 pages.
Quie et al., Coagulase-negative staphylococcal adherence and persistence. J Infect Dis. Oct. 1987;156(4):543-7.
Rogemond et al., Lectinlike adhesins in the Bacteroides fragilis group. Infect Immun. Jul. 1986;53(1):99-102.
Rohde et al., Structure, function and contribution of polysaccharide intercellular adhesin (PIA) to *Staphylococcus epidermidis* biofilm formation and pathogenesis of biomaterial-associated infections. Eur J Cell Biol. Jan. 2010;89(1):103-11. doi: 10.1016/j.ejcb.2009.10.005.
Roux et al., Magic bullets for the 21st century: the reemergence of immunotherapy for multi- and pan-resistant microbes. J Antimicrob Chemother. Dec. 2012;67(12):2785-7. doi: 10.1093/jac/dks335. Epub Aug. 16, 2012.
Rudikoff et al., Single amino acid substitution altering antigen-binding specificity. Proc Natl Acad Sci U S A. Mar. 1982;79(6):1979-83.
Rupp et al., Characterization of *Staphylococcus epidermidis* polysaccharide intercellular adhesin/hemagglutinin in the pathogenesis of intravascular catheter-associated infection in a rat model. Infect Immun. May 1999;67(5):2656-9.
Rupp et al., Characterization of the importance of polysaccharide intercellular adhesin/hemagglutinin of *Staphylococcus epidermidis* in the pathogenesis of biomaterial-based infection in a mouse foreign body infection model. Infect Immun. May 1999;67(5):2627-32.
Sack, Deadly Bacteria Found to Be More Common. New York Times. Oct. 17, 2007. Available at: http://www.nytimes.com/2007/10/17/health/17infect.html?pagewanted=prin. Last accessed Apr. 30, 2010. 3 pages.
Sadovskaya et al., Potential use of poly-N-acetyl-beta-(1,6)-glucosamine as an antigen for diagnosis of staphylococcal orthopedic-prosthesis-related infections. Clin Vaccine Immunol. Dec. 2007;14(12):1609-15. Epub Oct. 17, 2007.
Sanford et al., Detection of staphylococcal membrane receptors on virus-infected cells by direct adhesin overlay. Infect Immun. Jun. 1986;52(3):671-5.
Sanger et al., A microapparatus for liquid hydrogen fluoride solvolysis: sugar and amino sugar composition of Erysiphe graminis and Triticum aestivum cell walls. Anal Biochem. Jan. 1983;128(1):66-70.
Schumacher-Perdreau et al., Comparative analysis of a biofilm-forming *Staphylococcus epidermidis* strain and its adhesion-positive, accumulation-negative mutant M7. FEMS Microbiol Lett. Mar. 15, 1994;117(1):71-8.
Skurnik et al., Animal and human antibodies to distinct *Staphylococcus aureus* antigens mutually neutralize opsonic killing and protection in mice. J Clin Invest. Sep. 1, 2010;120(9):3220-33.
Skurnik et al., Targeting pan-resistant bacteria with antibodies to a broadly conserved surface polysaccharide expressed during infection. J Infect Dis. Jun. 2012;205(11):1709-18. Doi: 10.1093/infdis/jis254. Epub Mar. 23, 2012.
Skurnik et al., The exceptionally broad-based potential of active and passive vaccination targeting the conserved microbial surface polysaccharide PNAG. Expert Rev Vaccines. Aug. 2016;15(8):1041-53. doi: 10.1586/14760584.2016.1159135. Epub Mar. 16, 2016.
Soell et al., Capsular polysaccharide types 5 and 8 of *Staphylococcus aureus* bind specifically to human epithelial (KB) cells, endothelial cells, and monocytes and induce release of cytokines. Infect Immun. Apr. 1995;63(4):1380-6.
Soliman et al., Structural basis for antibody targeting of the broadly expressed microbial polysaccharide poly-N-acetylglucosamine. J Biol Chem. Apr. 6, 2018;293(14):5079-5089. doi: 10.1074/jbc.RA117.001170. Epub Feb. 15, 2018.

Sompolinsky et al., Encapsulation and capsular types in isolates of *Staphylococcus aureus* from different sources and relationship to phage types. J Clin Microbiol. Nov. 1985;22(5):828-34.
Sundgren et al., Varied presentation of the Thomsen-Friedenreich disaccharide tumor-associated carbohydrate antigen on gold nanoparticles. Carbohydr Res. Jul. 21, 2008;343(10-11):1594-604. doi: 10.106/j.carres.2008.05.003 Epub May 8, 2008.
Takeda et al., Protection against endocarditis due to *Staphylococcus epidermidis* by immunization with capsular polysaccharide/adhesin. Circulation. Dec. 1991;84(6):2539-46.
Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.
Thoma et al., Novel glycodendrimers self-assemble to nanoparticles which function as polyvalent ligands in vitro and in vivo. Angew Chem Int Ed Engl. Sep. 2, 2002;41(17):3195-8.
Thoma et al., Synthesis of oligosaccharide-polylysine conjugates: A well characterized sialyl lewis polymer for elisa. J Am Chem Soc. 1997;119(31):7414-5.
Thomas et al., Enzyme-linked lectinsorbent assay measures N-acetyl-D-glucosamine in matrix of biofilm produced by *Staphylococcus epidermidis*. Curr Microbiol. Oct. 1997;35(4):249-54.
Tojo et al., Isolation and characterization of a capsular polysaccharide adhesin from *Staphylococcus epidermidis*. J Infect Dis. Apr. 1988;157(4):713-22.
Tollersrud et al., Genetic and serologic evaluation of capsule production by bovine mammary isolates of *Staphylococcus aureus* and other *Staphylococcus* spp. from Europe and the United States. J Clin Microbiol. Aug. 2000;38(8):2998-3003.
Vershigora et al., Secretory antibodies to homologous and heterologous staphylococcal strains in the colostrum of rabbits. Zh Mikrobiol Epidemiol Immunobiol. 1980;88-90. Russian. 1 page.
Vlock et al., Abstracts of the 50th Interscience Conference on Antimicrobial Agents and Chemotherapy, Boston, MA, USA. Washington, DC, USA, American Society for Microbiology, Abstract G1-1654, p. 329, Sep. 12-15, 2010.
Von Eiff et al., Distribution of capsular and surface polysaccharide serotypes of *Staphylococcus aureus*. Diagn Microbiol Infect Dis. Jul. 2007;58(3):297-302. Epub Mar. 22, 2007.
Vuong et al., A crucial role for exopolysaccharide modification in bacterial biofilm formation, immune evasion, and virulence. J Biol Chem. Dec. 24, 2004;279(52):54881-6. Epub Oct. 22, 2004.
Wang et al., The pgaABCD locus of *Escherichia coli* promotes the synthesis of a polysaccharide adhesin required for biofilm formation. J Bacteriol. May 2004;186(9):2724-34.
Wessels et al., Isolation and characterization of type IV group B *Streptococcus* capsular polysaccharide. Infect Immun. Apr. 1989;57(4):1089-94.
Wessels et al., Structural properties of group B streptococcal type III polysaccharide conjugate vaccines that influence immunogenicity and efficacy. Infect Immun. May 1998;66(5):2186-92.
Wicken et al., Characterization of group N *Streptococcus* lipoteichoic acid. Infect Immun. May 1975;11(5):973-81.
Wray et al., Identification and characterization of a uroepithelial cell adhesin from a uropathogenic isolate of Proteus mirabilis. Infect Immun. Oct. 1986;54(1):43-9.
Wright et al., Preparation of synthetic glycoconjugates as potential vaccines against Shigella flexneri serotype 2a disease. Org Biomol Chem. May 21, 2004;2(10):1518-27. Epub Apr. 26, 2004.
Yamada, et al., Possible common biological and immunological properties for detecting encapsulated strains of *Staphylococcus epidermidis*. J Clin Microbiol. Oct. 1988;26(10):2167-72.
Yang et al., A practical synthesis of a (1-->6)-linked beta-D-glucosamine nonasaccharide. Carbohydr Res. Mar. 14, 2003;338(6):495-502.
Yang et al., Synthesis of (1-6)-β-D-glucosamine hexasaccharide, a potential antimumor and immunostimulating agent. Tetrahedron Lett. Oct. 2002;43:7561-3.
Yang et al., Synthesis of biantennary beta-D-(1-->6) glucosamine oligosaccharides. Carbohydr Res. Jun. 16, 2003;338(12):1313-8.

(56) References Cited

OTHER PUBLICATIONS

Yoshida et al., Cross protection between an encapsulated strain of *Staphylococcus hyicus* and an encapsulated strain of *Staphylococcus epidermidis*. Kansenshogaku Zasshi. May 1990;64(5):584-91. Japanese.

Yoshida et al., Cross protection between a strain of *Staphylococcus epidermidis* and eight other species of coagulase-negative staphylococci. Can J Microbiol. Jul. 1988;34(7):913-5.

Yoshida et al., Mouse virulent strain of *Staphylococcus epidermidis*. Relation of antiphagocytic activity to the protection-inducing antigen. Jpn J Microbiol. Jun. 1976;20(3):209-17.

Yoshida, et al., Immunological response to a strain of *Staphylococcus epidermidis* in the rabbit: production of protective antibody. J Med Microbiol. Nov. 1978;11(4):371-7. Abstract only.

Youmans, Staphylococci, Staphylococcal Disease, and Toxic Shock Syndrome. In: The Biologic and Clinical Basis of Infectious Diseases, Third Edition. Youmans et al., eds. W.B. Saunders Company: Philadelphia, 1985:618-29, 738-9.

Yudina et al., Synthesis of five nona-β-(1→6)-d-glucosamines with various patterns of N-acetylation corresponding to the fragments of exopolysaccharide of *Staphylococcus aureus*. Carbohydr Res. May 15, 2011;346(7):905-13. Epub Feb. 23, 2011.

Zeller et al., JAMA patient page. MRSA infections. JAMA. Oct. 17, 2007;298(15):1826.

Zhao et al., Efficacy of Antibody to PNAG Against Keratitis Caused by Fungal Pathogens. Invest Ophthalmol Vis Sci. Dec. 1, 2016;57(15):6797-6804. doi: 10.1167/iovs.16-20358.

Ziebuhr et al., A novel mechanism of phase variation of virulence in *Staphylococcus epidermidis*: evidence for control of the polysaccharide intercellular 19dhesion synthesis by alternating insertion and excision of the insertion sequence element IS256. Mol Microbiol. Apr. 1999;32(2):345-56.

Ziebuhr et al., Detection of the intercellular adhesion gene cluster (ica) and phase variation in *Staphylococcus epidermidis* blood culture strains and mucosal isolates. Infect Immun. Mar. 1997;65(3):890-6.

\* cited by examiner

SEQUENCE LISTING

<160> NUMBER OF SEQ ID NOS: 8

<210> SEQ ID NO 1
<211> LENGTH: 5
<212> TYPE: PRT

```
<213> ORGANISM: Artificial Sequence
<220> FEATURE:
<223> OTHER INFORMATION: Synthetic polypeptide

<400> SEQUENCE: 1

Gly Tyr Tyr Trp Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 2

Tyr Ile His Tyr Ser Arg Ser Thr Asn Ser Asn Pro Ala Leu Lys Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Asp Thr Tyr Tyr Tyr Asp Ser Gly Asp Tyr Glu Asp Ala Phe Asp Ile
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 4

Thr Leu Ser Ser Gly His Ser Asn Tyr Ala Ile Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 5

Val Asn Arg Asp Gly Ser His Ile Arg Gly Asp
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Gln Thr Trp Gly Ala Gly Ile Arg Val
1               5

<210> SEQ ID NO 7
<211> LENGTH: 124
<212> TYPE: PRT
<213> ORGANISM: Artificial Sequence
```

```
<220> FEATURE:
<223> OTHER INFORMATION: Synthetic polypeptide

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Ile His Tyr Ser Arg Ser Thr Asn Ser Asn Pro Ala Leu Lys
    50                  55                  60

Ser Arg Val Thr Ile Ser Ser Asp Thr Ser Lys Asn Gln Leu Ser Leu
65                  70                  75                  80

Arg Leu Ser Ser Val Thr Ala Ala Asp Thr Ala Val Tyr Tyr Cys Ala
                85                  90                  95

Arg Asp Thr Tyr Tyr Tyr Asp Ser Gly Asp Tyr Glu Asp Ala Phe Asp
            100                 105                 110

Ile Trp Gly Gln Gly Thr Met Val Thr Val Ser Ser
        115                 120

<210> SEQ ID NO 8
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 8

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Asn Tyr Ala
            20                  25                  30

Ile Ala Trp His Gln Gln Pro Gly Lys Gly Pro Arg Tyr Leu Met
        35                  40                  45

Lys Val Asn Arg Asp Gly Ser His Ile Arg Gly Asp Gly Ile Pro Asp
    50                  55                  60

Arg Phe Ser Gly Ser Thr Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Ala Gly Ile Arg Val Phe Gly Gly Gly Thr Lys Leu Thr Val Leu Gly
            100                 105                 110
```

POLYSACCHARIDE COMPOSITIONS FOR USE IN TREATING FILARIASIS

RELATED APPLICATIONS

This application is a national stage filing under 35 U.S.C. § 371 of international PCT application PCT/US2020/016863, filed Feb. 5, 2020, which claims the benefit under 35 U.S.C. § 119(e) of U.S. Provisional Application No. 62/801,399, filed Feb. 5, 2019, the entire contents of each of which are incorporated by reference herein.

FIELD OF DISCLOSURE

The present disclosure relates to the use of certain polysaccharide antigen and antibody compositions in the prevention and/or treatment of infections by filarial parasites (e.g., as a stand-alone therapy or as an adjunctive therapy to existing anti-filariasis medicaments).

BACKGROUND OF DISCLOSURE

Poly-N-acetyl glucosamine (PNAG) polysaccharide antigens are expressed on the surface of a number of different pathogens (e.g., bacteria, fungi, and protozoan parasites). PNAG and anti-PNAG antibody compositions have been used in the prevention and treatment of infection by such PNAG-expressing pathogens.

SUMMARY

The present disclosure is based, in part, on the unexpected and surprising finding that the polysaccharide poly N-acetyl glucosamine (PNAG) is expressed on the surface of filarial parasites. The disclosure therefore provides compositions comprising a PNAG-based polysaccharide, including oligosaccharide, vaccines (including conjugates, as described herein) or antibodies specific for PNAG for use in inducing immune responses against PNAG in a host and for preventing and/or treating infections by these PNAG-expressing filarial parasites.

PNAG expression in filarial parasites is particularly surprising since it has thus far only been identified in bacteria, fungi, and protozoan parasites. It is further unexpected that PNAG-based polysaccharide (e.g., oligosaccharide) vaccines and antibodies specific for PNAG are effective in killing filarial parasites, since filarial parasites are large organisms that cannot be ingested by phagocytes, the mechanism by which PNAG-expressing bacteria, fungi, and protozoan parasites are usually cleared. It was found surprisingly as described herein that anti-PNAG antibodies bind to the surface of the filarial parasites, thereby indicating that PNAG is expressed there, and that phagocytes are able to sufficiently damage the outer surface of the filarial parasites following such antibody binding, causing them to release their intracellular contents, leading to eventual death of such parasites. The anti-PNAG antibody and phagocytes, including polymorphonuclear neutrophils (PMN), are believed to effect the observed killing through a process called trogocytosis.

Thus, provided herein is a method for treating a subject having or at risk of developing filariasis, comprising administering to a subject having or at risk of developing filariasis deacetylated poly-N-acetyl glucosamine (dPNAG) conjugated to a carrier compound in an effective amount to induce an immune response against dPNAG and PNAG.

Also provided herein is a method for treating a subject having or at risk of developing filariasis, comprising administering to a subject having or at risk of developing filariasis a deacetylated poly-N-acetyl glucosamine (dPNAG) conjugated to a carrier compound in an effective amount to treat or prevent filariasis in the subject.

Also provided herein is a method for treating a subject having or at risk of developing filariasis, comprising administering to a subject having or at risk of developing filariasis an isolated polysaccharide having the formula

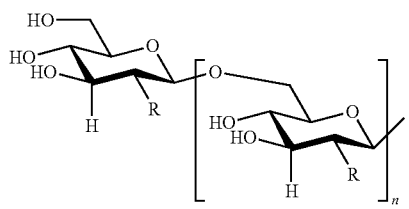

wherein n is at least 4, R is selected from the group consisting of —NH—CO—CH$_3$ and —NH$_2$, provided that less than 50% of the R groups are —NH—CO—CH$_3$, in an amount effective to induce an immune response against the polysaccharide and against poly-N-acetyl glucosamine (PNAG).

Also provided herein is a method for treating a subject having or at risk of developing filariasis, comprising administering to a subject having or at risk of developing filariasis a polysaccharide conjugated to a carrier compound, wherein the polysaccharide has the formula

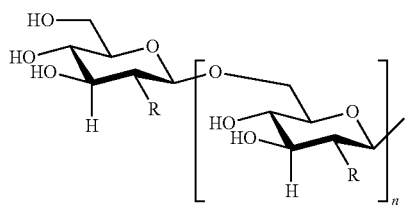

wherein n is at least 4, R is selected from the group consisting of —NH—CO—CH$_3$ and —NH$_2$, provided that less than 50% of the R groups are —NH—CO—CH$_3$, in an amount effective to induce an immune response against the polysaccharide and against poly-N-acetyl glucosamine (PNAG).

Various embodiments are provided relating to the methods described herein. These are recited below.

In some embodiments, the dPNAG or polysaccharide is conjugated to the carrier compound through a linker. In some embodiments, the linker comprises a structure of:

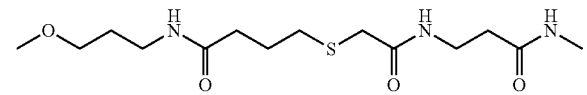

In some embodiments, the carrier compound is a peptide or protein carrier. In some embodiments, the peptide or protein carrier is or comprises a tetanus toxoid.

In some embodiments, less than 30%, less than 20%, less than 10%, or less than 5% of R groups are —NH—CO—

CH$_3$. In some embodiments, none of the R groups is —NH—CO—CH$_3$. In some embodiments, the R group is —NH$_2$.

In some embodiments, n is 4. In some embodiments, n is 5. In some embodiments, n is 4, 5, 6, 7, or 8. In some embodiments, n is 9. In some embodiments, n is 10, 11, 12, 13 or 14. In some embodiments, n is at least 15, at least 20, at least 50, at least 100, at least 200, at least 300, at least 400 or at least 500. In some embodiments, n is 15, 20, 50, 100, 200, 300, 400 or 500.

In some embodiments, dPNAG or the polysaccharide has a molecular weight of 400-500,000 Daltons.

In some embodiments, a plurality of dPNAG or polysaccharides are conjugated to the carrier compound, optionally wherein the carrier compound is a peptide or protein carrier, further optionally wherein the peptide or protein carrier is tetanus toxoid.

In some embodiments, the subject is human. In some embodiments, the filariasis (elephantiasis) is caused by *Wuchereria bancrofti, Brugia malayi, Brugia timori, Mansonella streptocerca, Onchocerca volvulus, Loa loa, Mansonella perstans,* or *Mansonella ozzardi.*

In some embodiments, the subject is an agricultural animal. In some embodiments, the subject is a zoo animal. In some embodiments, the subject is a companion animal. In some embodiments, the companion animal is a dog or a cat. In some embodiments, the subject is a horse, cow, swine, goat, or sheep.

In some embodiments, the filariasis is caused by *Dirofilaria immitis, Acanthocheilonema* spp., or *Brugia* spp. In some embodiments, the filariasis is caused by *Dirofilaria immitis*. In some embodiments, the *Dirofilaria immitis* is resistant to an anti-filariasis medicament. In some embodiments, the *Dirofilaria immitis* is resistant to ivermectin, avermectin, and/or milbemycin.

In some embodiments, dPNAG or the polysaccharide, conjugated or unconjugated, is administered with an adjuvant.

In some embodiments, dPNAG or the polysaccharide, conjugated or unconjugated, is administered systemically. In some embodiments, dPNAG or the polysaccharide, conjugated or unconjugated, is administered locally.

In some embodiments, the subject is at risk of developing filariasis. In some embodiments, the subject has filariasis. In some embodiments, the subject is receiving or has received an anti-filariasis medicament. In some embodiments, the anti-filariasis medicament is selected from diethylcarbamazine (DEC), macrocyclic lactones, and tetracycline. In some embodiments, the macrocyclic lactones is selected from ivermectin, avermectin, and milbemycin.

Also provided herein is a pharmaceutical composition comprising an isolated polysaccharide having the formula

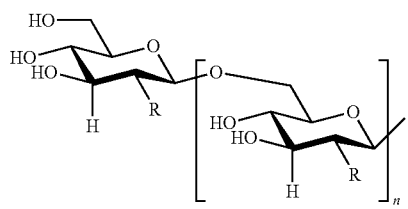

wherein n is at least 4, R is selected from the group consisting of —NH—CO—CH$_3$ and —NH$_2$, provided that less than 50% of the R groups are —NH—CO—CH$_3$, for use in treating or preventing filariasis in a subject.

Also provided herein is a pharmaceutical composition comprising a polysaccharide-carrier conjugate, wherein the polysaccharide has the formula

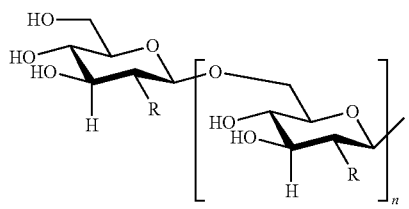

wherein n is at least 4, R is selected from the group consisting of —NH—CO—CH$_3$ and —NH$_2$, provided that less than 50% of the R groups are —NH—CO—CH$_3$, for use in treating or preventing filariasis in a subject.

Also provided herein is a pharmaceutical composition comprising an isolated polysaccharide having the formula

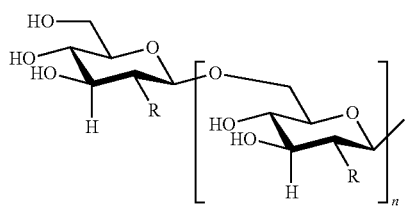

wherein n is at least 4, R is selected from the group consisting of —NH—CO—CH$_3$ and —NH$_2$, provided that less than 50% of the R groups are —NH—CO—CH$_3$, for use in inducing an immune response against the polysaccharide and against poly-N-acetyl glucosamine (PNAG) in a subject having or at risk of developing filariasis.

Also provided herein is a pharmaceutical composition comprising a polysaccharide-carrier conjugate, wherein the polysaccharide has the formula

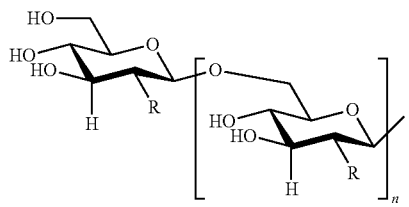

wherein n is at least 4, R is selected from the group consisting of —NH—CO—CH$_3$ and —NH$_2$, provided that less than 50% of the R groups are —NH—CO—CH$_3$, for use in inducing an immune response against the polysaccharide against poly-N-acetyl glucosamine (PNAG) in a subject having or at risk of developing filariasis.

Also provided herein is a method for treating a subject having or at risk of developing filariasis comprising administering to a subject having or at risking of developing filariasis an antibody or antibody fragment that binds to poly-N-acetyl glucosamine (PNAG) and deacetylated PNAG (dPNAG) in an amount effective to induce an immune response against PNAG.

In some embodiments, the antibody or antibody fragment is F598 (ATCC PTA-5931) antibody or a fragment thereof.

In some embodiments, the antibody or antibody fragment is conjugated to an agent. In some embodiments, the agent is a cytotoxic agent.

In some embodiments, the subject is human. In some embodiments, the filariasis is caused by *Wuchereria bancrofti*, *Brugia malayi*, *Brugia timori*, *Mansonella streptocerca*, *Onchocerca volvulus*, *Loa loa*, *Mansonella perstans*, or *Mansonella ozzardi*.

In some embodiments, the subject is an agricultural animal. In some embodiments, the subject is a zoo animal. In some embodiments, the subject is a companion animal. In some embodiments, the companion animal is a dog or a cat. In some embodiments, the subject is a horse, cow, swine, goat, or sheep.

In some embodiments, the filariasis is caused by *Dirofilaria immitis*, *Acanthocheilonema* spp., or *Brugia* spp. In some embodiments, the filariasis is caused by *Dirofilaria immitis*. In some embodiments, the *Dirofilaria immitis* is resistant to an anti-filariasis medicament. In some embodiments, the *Dirofilaria immitis* is resistant to ivermectin, avermectin, and/or milbemycin.

In some embodiments, the antibody or antibody fragment is administered systemically. In some embodiments, the antibody or antibody fragment is administered locally.

In some embodiments, the subject is at risk of developing filariasis. In some embodiments, the subject has filariasis. In some embodiments, the subject is receiving or has received an anti-filariasis medicament. In some embodiments, the anti-filariasis medicament is selected from diethylcarbamazine (DEC), macrocyclic lactones, and tetracycline. In some embodiments, the macrocyclic lactones are selected from ivermectins, avermectins and milbemycins.

Also provided herein is a pharmaceutical composition comprising an antibody or antibody fragment that binds to PNAG and dPNAG for use in treating or preventing filariasis in a subject.

Also provided herein is a pharmaceutical composition comprising an antibody or antibody fragment that binds to PNAG and dPNAG for use in inducing an immune response against PNAG in a subject having or at risk of developing filariasis.

In some embodiments, the antibody or antibody fragment is monoclonal antibody F598 or an antigen-binding fragment thereof.

Also provided herein is a method of treating or preventing *Dirofilaria immitis* infection in a dog or a cat, comprising administering to the dog or the cat an effective amount of an isolated polysaccharide having the formula

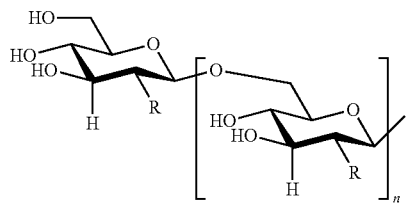

wherein n is at least 4, R is selected from the group consisting of —NH—CO—CH$_3$ and —NH$_2$, provided that less than 50% of the R groups are —NH—CO—CH$_3$.

Also provided herein is a method of treating or preventing *Dirofilaria immitis* infection in a dog or a cat, comprising administering to the dog or the cat an effective amount of a polysaccharide-carrier conjugate, wherein the polysaccharide has the formula

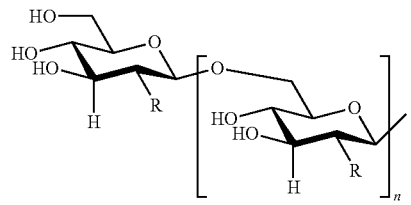

wherein n is at least 4, R is selected from the group consisting of —NH—CO—CH$_3$ and —NH$_2$, provided that less than 50% of the R groups are —NH—CO—CH$_3$.

Also provided herein is a method of treating or preventing *Dirofilaria immitis* infection in a dog or a cat, comprising administering to the dog the cat an effective amount of an antibody or antibody fragment that binds to PNAG and dPNAG.

In some embodiments, the foregoing methods further comprise administering an anti-filariasis medicament to the dog or the cat.

In some embodiments, the antibody or antibody fragment is monoclonal antibody F598 or an antigen-binding fragment thereof.

This disclosure contemplates use of the polysaccharides (including oligosaccharides) provided herein, whether in conjugated or unconjugated form, and/or the anti-PNAG antibodies provided herein to target filarial parasites at one or more stages of development including for example at the larval stage (e.g., L3 and/or L4 stage), the developing adult stage, and/or at the mature adult stage.

Each of the limitations of the disclosure can encompass various embodiments of the disclosure. It is therefore anticipated that each of the limitations of the disclosure involving any one element or combinations of elements can be included in each aspect of the disclosure.

BRIEF DESCRIPTION OF THE FIGURES

(FIG. 2A) Synthesis of the dPNAG-tetanus toxoid (TT) conjugate vaccine. SBAP stands for succinimidyl 3-(bromoacetamido) propionate. TCEP stands for Tris (2-carboxyethyl) phosphine hydrochloride. (FIG. 2B) Tetanus toxoid with multiple dPNAG polysaccharide conjugated denoted as -[GlcNH$_2$]$_5$ and N-conjugated to the tetanus toxoid through a linker.

(FIG. 4A) Male *Dirofilaria immitis*. (FIG. 4B) Female *Dirofilaria immitis*. Color versions of the Figures are available upon request.

DETAILED DESCRIPTION OF CERTAIN EMBODIMENTS

Figure 1:
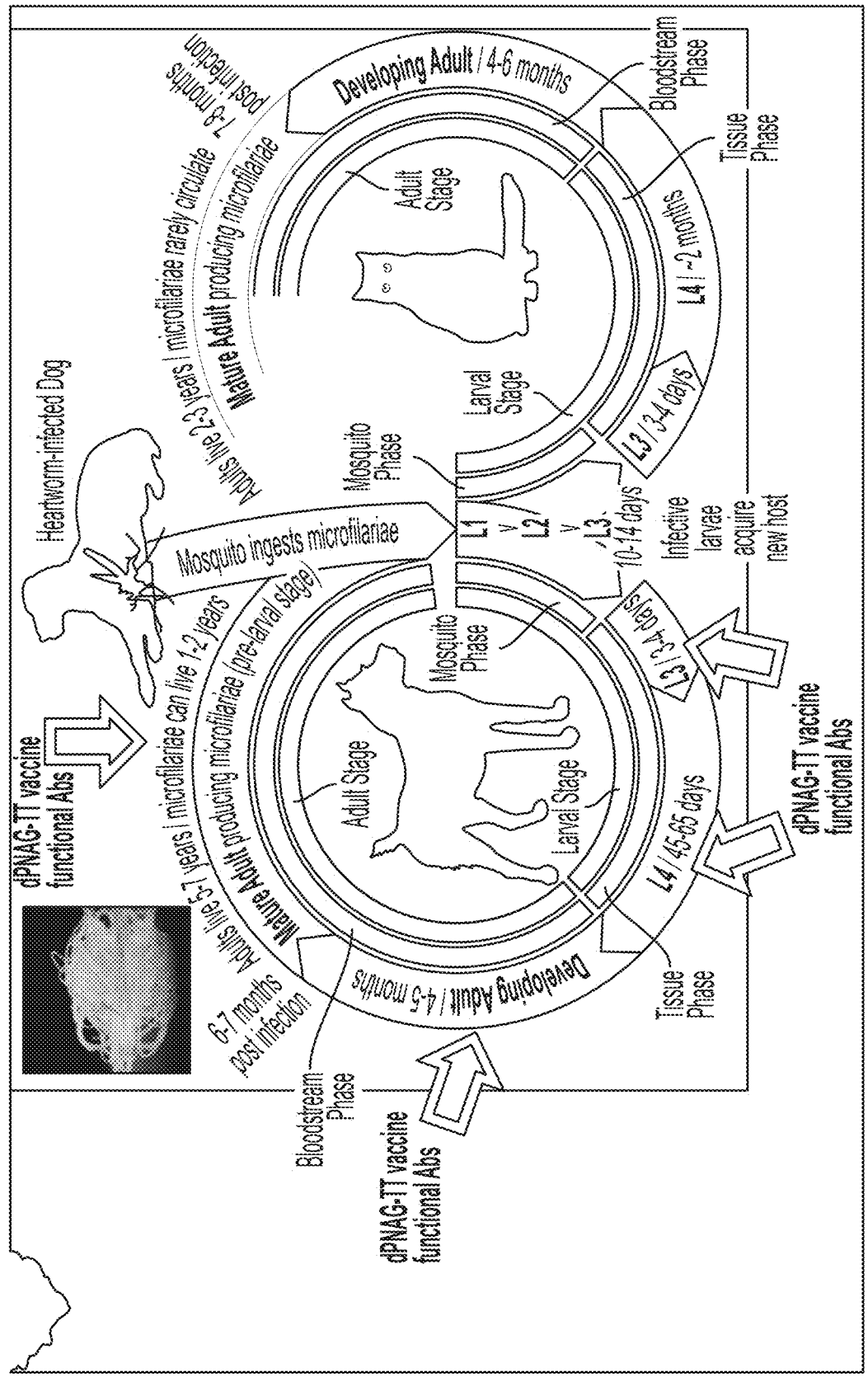
FIG. 1 is a schematic showing the infection routes of *Dirofilaria immitis* and the use of dPNAG-tetanus toxoid (TT) conjugate vaccine at different stages of *Dirofilaria immitis* life cycle. The vaccine may be used prophylactically.

The disclosure relates, in part, to the unexpected finding of PNAG expression in filarial parasites. The finding was unexpected because PNAG has thus far only been found on the surface of bacteria, fungi, and protozoan parasites. Further, heretofore, it was unclear whether PNAG-based polysaccharide vaccines, such as polysaccharide-conjugate vaccines, or PNAG-specific antibodies (also referred to herein as anti-PNAG antibodies) would be effective in killing filarial parasites. This is because filarial parasites are large organisms that presumably cannot be ingested by phagocytes, yet phagocytosis is typically the mechanism by which bacteria, fungi, and protozoan parasites are usually cleared. This disclosure is therefore further premised in part on the surprising finding that PNAG-specific antibodies bind to the surface of filarial parasites, thereby evidencing that PNAG is expressed by the filarial parasites, and that phagocytes are able to sufficiently damage the outer surface of the filarial parasites as a result of such antibody binding, thereby causing release of the intracellular contents and ultimately death of the filarial parasites.

The finding that filarial parasites express PNAG provides new approaches for preventing and/or treating infections caused by such parasites. Thus, the disclosure contemplates the use of PNAG, deacetylated forms of PNAG referred to herein as dPNAG, PNAG- and dPNAG-based polysaccharide conjugates, and/or PNAG-specific antibodies, including antibodies that bind to both PNAG and dPNAG, in stimulating immune responses against PNAG, and preventing and treating infections by PNAG-expressing filarial parasites (i.e., filariasis).

Filarial Parasites

Filarial parasites are a superfamily of highly specialized parasitic nematodes. Infections with filarial parasites cause conditions generically referred to as filariasis. The definitive host for filarial parasites is a vertebrate, e.g., a mammal, bird, reptile or amphibian. The intermediate host is an arthropod (e.g., a fly or a mosquito).

Mature filarial parasites live in body fluids, bodily cavities, or particular tissues depending on the particular definitive host. For example, some filarial parasites, including without limitation *Wuchereria bancrofti*, *Brugia malayi*, and *Brugia timori*, invade lymphatic vessels and in some instances may be so numerous as to clog such vessels, thereby causing lymphatic filariasis. As another example, some filarial parasites, including without limitation, *Loa loa*, *Mansonella streptocerca*, and *Onchocerca volvulus*, invade subcutaneous connective tissues, thereby causing subcutaneous filariasis. Still other filarial parasites, including without limitation, *Mansonella perstans*, *Mansonella ozzardi*, and *Dirofilaria immitis*, invade serous cavities of the abdomen (e.g., the lungs, pleural cavity, or pericardial cavity), thereby causing serous cavity filariasis.

Wherever established, filarial parasites may survive for years, with the fertilized females continuously producing motile embryos called microfilariae (instead of eggs). The adult parasites usually remain in one tissue and release early larval forms called microfilariae into the host's bloodstream. These circulating microfilariae can be taken up with a blood meal by the arthropod vector; in the vector, they develop into infective larvae that can be transmitted to a new host.

A microfilaria cannot reproduce in the definitive host and cannot infect another definitive host directly, and rather must make its way through the host's body to where an intermediate host that acts as a vector can swallow it while itself acting as an ectoparasite to the definitive host. It must succeed in invading its vector organism fairly soon, because, unlike adult filarial worms, microfilariae only survive for a few months to a year or two depending on the species and they develop no further unless they are ingested by a suitable blood-feeding female insect.

In the intermediate host (e.g., a fly or a mosquito), the microfilaria may further develop until transmission occurs via the vector to another definitive host. In the new definitive host, the microfilaria develop into the final stage of sexual maturity. The mature filarial parasite then must mate before a female can produce the next generation of microfilariae; in other words, invasion by a single worm cannot produce an infection. As a result, it may take years of exposure to infections before a serious disease condition can develop in a host.

Once a new generation of microfilariae is released in the definitive host, it must find host tissue suited to the nature of the vector species. For example, if the vector is a skin-piercing fly such as a mosquito, the microfilaria must enter the peripheral blood circulation. Species that use skin-rasping flies such as Simuliidae and skin-cutting flies such as Tabanidae typically home to hypodermal tissues. Still other species appear to migrate daily to bodily regions favored by the vector ectoparasites.

Thus far, there are eight known filarial parasites that use humans as their definitive hosts. These are *Wuchereria bancrofti, Brugia malayi, Brugia timori, Mansonella streptocerca, Onchocerca volvulus, Loa loa, Mansonella perstans*, and *Mansonella ozzardi*.

Other definitive hosts for filarial parasites include companion animals (e.g., horse, cow, swine, goat, sheep, dog, or cat) or zoo animals (e.g., a canine or feline zoo animal). Such filarial parasites include, without limitation, *Dirofilaria immitis, Acanthocheilonema* spp., and *Brugia* spp.

The present disclosure, in some aspects, provides compositions and methods for inducing an immune response against PNAG in a subject having or at risk of developing filariasis caused by any filarial parasite including but not limited to those listed above. The compositions and methods can therefore be used to treat filariasis in the subject. In some embodiments, the filariasis is caused by a human filarial parasite in a human subject. In some embodiments, the filariasis is caused by a filarial parasite in a canine subject.

In some embodiments, the filariasis is caused by *Dirofilaria immitis*. *Dirofilaria immitis*, also known as heartworm, is spread from host to host through the bites of mosquitoes. The definitive host for *Dirofilaria immitis* is the dog, but it can also infect cats, wolves, coyotes, jackals, foxes, and other animals, such as ferrets, bears, seals, sea lions and even, under very rare circumstances, humans.

Heartworms go through several life stages before they become adults capable of infecting the pulmonary artery of the host animal. The worms require the mosquito as an intermediate stage to complete their lifecycles. The rate of development in the mosquito is temperature-dependent, requiring about two weeks of temperature at or above 27° C. (80° F.). Below a threshold temperature of 14° C. (57° F.), development cannot occur, and the cycle is halted. As a result, transmission is limited to warm weather, and duration of the transmission season varies geographically. The period between the initial infection when the dog is bitten by a mosquito and the maturation of the worms into adults living in the heart takes six to seven months in dogs and is known as the "prepatent period."

After infection, the third-stage larval heartworms (L3) deposited by the mosquito grow for a week or two and molt to the fourth larval stage (L4) under the skin at the site of the mosquito bite. Then, they migrate to the muscles of the chest and abdomen, and 45 to 60 days after infection, molt to the fifth stage (L5, immature adult). Between 75 and 120 days after infection, these immature heartworms then enter the bloodstream and are carried through the heart to reside in the pulmonary artery. Over the next three to four months, they increase greatly in size. The female adult worm is about 30 cm in length, and the male is about 23 cm, with a coiled tail. By seven months after infection, the adult worms have mated and the females begin producing microfilariae.

The microfilariae circulate in the bloodstream for as long as two years, waiting for the next stage in their lifecycles in the gut of a bloodsucking mosquito. When ingested by a mosquito, the microfilariae undergo a series of molts to the infective third larval stage, and then migrate to the salivary glands of the mosquito, where they wait to infect another host. The incubation period required to reach the stage where the microfilariae become transmittable to another host can be as little as two weeks or as long as six weeks, depending on the warmth of the climate, and the larval lifecycle ceases entirely if the ambient temperature drops below 14° C. (57° F.).

Heart filariasis caused by *Dirofilaria immitis* in dogs or cats is prevalent in the United States. According to the American Heartworm Society, the average number of dogs diagnosed with heart filariasis per clinic in 2016 rose by 21.7% since 2013. Currently available preventive therapeutics for *Dirofilaria immitis* infection are effective. However, poor compliance often leads to sustained high *Dirofilaria immitis* infection rates. Further, *Dirofilaria immitis* strains that have developed resistance to existing treatments (e.g., ivermectins, avermectins, and/or milbemycins) have been reported.

The compositions and methods described herein are shown to kill L1 and L3 stage *Dirofilaria immitis* (e.g., see FIGS. 5-9) as well as L3 stage *B. malayi* (FIG. 11) and may be used as a standard alone therapy or an adjunctive preventive therapies against filariasis caused by *Dirofilaria immitis* and other parasites such as *B. malayi*. The new treatment strategies described herein may address compliance issues and battling the rise of drug resistant parasite strains such as but not limited to *Dirofilaria immitis* drug resistant strains.

PNAG and dPNAG

The PNAG polysaccharide is a poly N-acetyl beta ((3) 1-6 glucosamine (i.e., it is comprised of glucosamine monomer units linked together by beta ((3) 1-6 linkages). The acetyl group, when present, is N-linked to the glucosamine monomer (as opposed to being O-linked). PNAG has the structure of the following formula

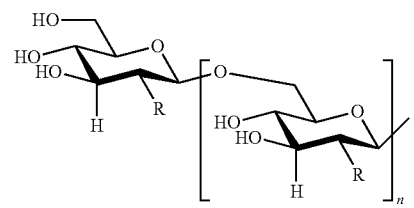

where n is an integer, and R is selected from the group consisting of —NH—CO—CH$_3$ and —NH$_2$. "n" may range, without limitation, from 2-500. In some embodiments, n is greater than 500. In some embodiments, n is 4, 5, 6, 7, 8, 9 or 10.

In some embodiments, n is 2-500, 2-450, 2-400, 2-350, 2-300, 2-250, 2-200, 2-150, 2-100, 2-50, 2-40, 2-30, 2-20, 2-10, 4-500, 4-450, 4-400, 4-350, 4-300, 4-250, 4-200, 4-150, 4-100, 4-50, 4-40, 4-30, 4-20, 4-10, 5-500, 5-450, 5-400, 5-350, 5-300, 5-250, 5-200, 5-150, 5-100, 5-50, 5-40, 5-30, 5-20, 5-10, 10-500, 10-500, 10-450, 10-400, 10-350, 10-300, 10-250, 10-200, 10-150, 10-100, 10-50, 10-40, 10-30, 10-20, 20-500, 20-450, 20-400, 20-350, 20-300, 20-250, 20-200, 20-150, 20-100, 20-50, 20-40, 20-30, 30-500, 30-450, 30-400, 30-350, 30-300, 30-250, 30-200, 30-150, 30-100, 30-50, 30-40, 40-500, 40-450, 40-400, 40-350, 40-300, 40-250, 40-200, 40-150, 40-100, 40-50, 50-500, 50-450, 50-400, 50-350, 50-300, 50-250, 50-200, 50-150, 50-100, 100-500, 100-450, 100-400, 100-350, 100-300, 100-250, 100-200, 100-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-45-, 350-400, 400-500, 400-450, or 450-500. In some embodiments, n is equal to or at least 5, 10, 15, 20, 50, 100, 150, 200, 250, 300, 350, 400, 450, or 500. In some embodiments, n is at least 4 (e.g., 4, 5, 6, 7, 8, or more). In some embodiments, n is 5.

It was previously described (e.g., in PCT Application Publication Nos. WO 2004/043405 and WO 2005/103084, incorporated herein by reference) that poorly acetylated forms of PNAG (less than 50% acetylation) are highly immunogenic and better able to elicit opsonic protective antibodies as compared to highly acetylated forms of PNAG, having 50% or greater acetylation, in in vivo immune stimulation assays. The antibodies elicited following dPNAG administration recognize dPNAG and, typically, the highly acetylated forms of PNAG also. These findings made the poorly acetylated form of PNAG a suitable vaccine candidate for stimulating protective immune responses in vivo.

As a result, the present disclosure also contemplates the use of the poorly acetylated forms of PNAG to stimulate active immunity in subjects. Such poorly acetylated forms of PNAG are referred to herein as deacetylated PNAG (or dPNAG). dPNAG has the same structure as that shown above with the exception that less than 50% of the R groups are —NH—CO—CH$_3$ (i.e., less than 50% of the amino groups are substituted with acetate). dPNAG may be wholly or partially deacetylated, provided that the range of acetylation is from 0 to less than 50%. Wholly deacetylated dPNAG (i.e., where R=NH$_2$ only, none of the R groups is —NH—CO—CH$_3$) may be referred to herein as a dPNAG homopolymer. Partially deacetylated dPNAG (i.e., wherein R may be —NH$_2$ or —NH—CO—CH$_3$, provided that less than 50% of R groups are —NH—CO—CH$_3$) may be referred to herein as a dPNAG heteropolymer. For instance, less than 49%, less than 45%, less than 40%, less than 35%, less than 30%, less than 25%, less than 20%, less than 15%, less than 10%, less than 5%, or less than 1% of R groups may be —NH—CO—CH$_3$. In some instances, the level of acetylation is 40% or less, 35% or less, 20% or less, or 15% or less. In some instances, the level of acetylation is 0%. In some instances, the level of acetylation is 0% and n is 5 or greater.

The disclosure contemplates the use of highly acetylated and poorly acetylated forms of PNAG in various applications. As a non-limiting example, highly acetylated PNAG may be used for making antibodies to be used as a diagnostic or for another non-therapeutic purpose.

Unless indicated otherwise, the term PNAG is used to refer to the highly acetylated form of the polysaccharide. Such form has 50% or greater level of acetylation.

The disclosure contemplates use of naturally occurring forms of PNAG, as well as synthetic forms of PNAG (i.e., those made completely de novo). As will be appreciated, such synthetic forms can be synthesized with a known number and sequence glucosamine and N-acetyl glucosamine units that are β-1-6 linked to each other. The synthetic forms may be as small as 4 monomers in some instances.

The disclosure contemplates use of dPNAG that is synthesized de novo or that is produced by deacetylation of PNAG, including deacetylation of naturally occurring PNAG. dPNAG may be 2, 3, 4, 5, or more monomers in length and as described herein may have 0% to less than 50% acetylation. PNAG or dPNAG may be used in a conjugate form. PCT Application Publication No. WO 2010/011284 and U.S. Patent Application Publication No. US 20110150880 describe synthetic oligosaccharides, their synthesis, and their conjugation to carriers. The specific and entire teachings of these references are incorporated by reference herein. Virtually any linker may be used to conjugate dPNAG oligosaccharide (e.g., a 5-mer) to another compound such as but not limited to a carrier compound (e.g., a protein or peptide carrier compound). A plurality of dPNAG oligosaccharides may be conjugated to a carrier compound, such that the ratio of carrier compound to dPNAG oligosaccharides may range from 1:2 to 1:100, including without limitation 1:2, 1:3, 1:4, 1:5, 1:6, 1:7, 1:8, 1:9, 1:10, 1:15, 1:20, 1:25, 1:30, 1:35, 1:40, 1:50, 1:60, 1:70, 1:80, 1:90 and 1:100. A variety of carrier compounds are available and suitable, including without limitation protein carrier compounds such as tetanus toxoid, as discussed in greater detail below. Similar embodiments apply to PNAG conjugates.

An example of a conjugate is an oligosaccharide-carrier conjugate comprising an oligosaccharide (such as dPNAG) conjugated to a carrier (such as tetanus toxoid) through a linker that is

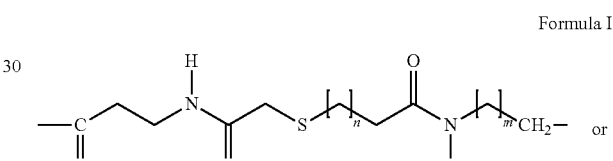

Formula I

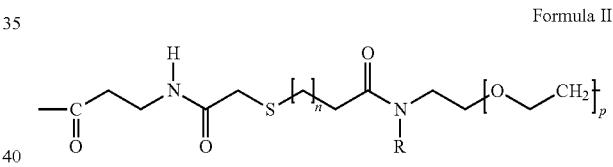

Formula II wherein n is greater than 1, m is a number selected from 1 to 10, p is a number selected from 1 to 20, and R is H or an alkyl group, and wherein the linker is O-linked to the oligosaccharide and N-linked to the carrier. "n" may be 2-10, 2-5, or 2, 3, or 4, in some embodiments.

In some embodiments, the linker has a structure of:

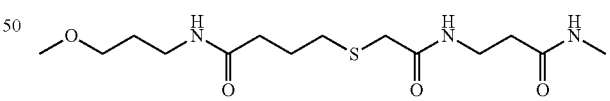

An intermediate of such a conjugate may be an oligosaccharide bearing an O-linked linker, wherein the linker comprises Formula III

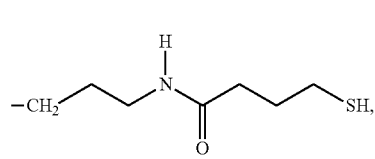

wherein the oligosaccharide is a β-1-6 linked glucosamine that is 2-20 monomers in length, or 5-11 monomers in length, or 5 monomers in length, or 9 monomers in length, for example. The size of PNAG and dPNAG may vary and may be dictated by the particular application. In some embodiments, PNAG and dPNAG molecular weight may range from about 400 Daltons (Da) to 750 kiloDaltons (kDa). In some embodiments, PNAG or dPNAG has a molecular weight of 600-500,000 Daltons. In some embodiments, PNAG or dPNAG has a molecular weight of less than 2 kDa. In some embodiments, the molecular weight of PNAG or dPNAG may be at least about 2200 Daltons, or at least about 2500 Daltons, or at least about 3000 Daltons. In some embodiments, PNAG or dPNAG may be 5 monomers, 6 monomers, 7 monomers, 8 monomers, 9 monomers, 10 monomers, 12 monomers, or 15 monomers in length. In other embodiments, PNAG or dPNAG has a molecular weight of at least 100 kDa, optionally in the range of 100-500 kDa.

As discussed in greater detail herein, PNAG and dPNAG, including lower molecular weight versions of PNAG and dPNAG, may be conjugated to a carrier such as a carrier protein (e.g., tetanus toxoid). When conjugated to a carrier, PNAG and dPNAG may be as small as 2-3 monomer units or it may be at least 4-6 monomer units in length, or it may be longer. Polysaccharides between 400 Da and 1,000 kDa may be typical, in some embodiments. PNAG or dPNAG forms of this size may be synthesized de novo as described herein. When used without a carrier compound, in some embodiments, the PNAG or dPNAG may be about 100 kDa or greater.

The disclosure contemplates the use of naturally occurring PNAG and synthetic forms of PNAG and dPNAG. PNAG may be isolated or derived from any PNAG-expressing pathogen such as but not limited to the filarial parasites described herein.

PNAG and dPNAG antigens may be provided and/or used in isolated form. An isolated polysaccharide is one that has been removed and thus separated at least in part from the environment in which it normally exists or in which it has been synthesized. In some instances, an isolated polysaccharide is sufficiently separated from other compounds to be characterized structurally or functionally. For example, an isolated polysaccharide may be "sequenced" in order to determine its chemical composition. In the case of dPNAG, it may be isolated from all components used to synthesize this oligosaccharide in vitro.

dPNAG may be produced by deacetylating PNAG forms, including those that occur naturally, using methods described herein. dPNAG that is synthesized in vitro may also be isolated from its synthesis reaction mixture, thereby separating it from reaction substrates, enzymes, co-factors, catalysts, or spurious reaction products.

In some embodiments, PNAG may be prepared from a number of pathogens that are known to express PNAG. These include without limitation S. epidermis and S. aureus. Specific strains include S. epidermis RP62A (ATCC number 35984), S. epidermis RP12 (ATCC number 35983), S. epidermis M187, S. aureus RN4220 (pCN27), S. aureus MN8 mucoid, and S. carnosus TM300 (pCN27).

PNAG can be obtained from naturally occurring sources by a variety of methods including extracting a crude PNAG preparation from a microbial culture, including cells and cell free culture supernatants, resulting in the isolation of a high molecular weight PNAG-enriched material from the crude PNAG preparation, and obtained initially by precipitating an impure PNAG containing the high molecular weight PNAG-enriched material with a solvent such as methanol, ethanol, acetone or any other organic solvent known to one skilled in the art as being capable of causing the precipitation of polysaccharides from aqueous solutions. The steps of extracting the crude PNAG preparation and isolating and precipitating the impure PNAG preparation may be performed using methods known in the art and described in published U.S. application No. US-2005-0118198-A1.

This impure PNAG material then may be purified and de-acetylated to produce dPNAG. De-acetylation may be carried out chemically or enzymatically. Chemical deacetylation, in some instances, may involve incubating impure PNAG preparation with a base or acid to produce a semi-pure PNAG preparation, neutralizing the preparation, and further treating the neutralized preparation to produce dPNAG.

Enzymatic deacetylation typically involves incubating impure PNAG with enzymes, such as bacterial enzymes, that digest biological materials, including cell-wall disrupting agents such as lysozyme, lysostaphin, and proteinase K, and nuclease enzymes such as DNase and RNase to digest DNA and RNA. This is followed by an addition of a solvent that will precipitate PNAG out of solution, collection of the precipitate and re-dissolution of PNAG in a base, such as NaOH or an acid such as HCl, followed by neutralization. The neutralization can be accomplished using a base if the incubation step was performed with an acid, or with an acid if the incubation step was performed with a base. The insoluble fraction from the neutral material is then treated, e.g., by incubation in hydrofluoric acid to produce a pure PNAG antigen or by re-dissolution in buffers with a pH<4.0 followed by molecular sieve and/or ion-exchange chromatography.

Another isolation method includes the steps of extracting a crude PNAG suspension from a microbial (including bacterial) culture by incubating the culture with a strong base or acid. Preferably, the culture is stirred in the strong base or acid for at least 2 hours, and more preferably at least 5, 10, 15, 18 or 24 hours. The strong base or acid can be any type of strong base or acid, but preferably has a strength of at least 1 M NaOH or HCl. In some embodiments, the strong base or acid is 5 M NaOH or 5 M HCl. The acid or base solution is then subjected to centrifugation to collect the cell bodies. In some embodiments, the extraction procedure is repeated several times. The resultant acid or base solution is neutralized to approximately pH 7 and then dialyzed to produce insoluble impure PNAG.

dPNAG can also be synthesized de novo. Methods for de novo synthesis of dPNAG are described in published U.S. patent application Nos. US-2005-0118198-A1 and US-2011-0150880-A1.

Some methods may produce dPNAG from starting materials such as but not limited to polyglucose (i.e., dextran), polyglucosamines such as chitin or chitosan, polyglucosaminouronic acid, and polygalactosaminouronic acid.

PNAG and dPNAG preparations may be of varying purity. As used herein, a pure PNAG or dPNAG preparation is a PNAG or dPNAG preparation that is greater than 92% free of contaminants. These contaminants may include galactose, phosphate, teichoic acid, and the like. In some embodiments, PNAG and dPNAG compositions are at least 93%, 94%, 95%, 96%, 97%, 98%, 99% free of contaminants or are 100% free of contaminants. In some embodiments, a dPNAG composition is free of highly acetylated PNAG.

The degree of purity of a PNAG or a dPNAG composition can be assessed by any means known in the art. For example, the purity can be assessed by chemical analysis assays as well as gas chromatography and nuclear magnetic resonance to verify structural aspects of the material.

Carriers

PNAG and dPNAG, whether synthesized de novo or produced directly or indirectly from a naturally occurring source, may be used in a conjugated or an unconjugated form. In a conjugated form, PNAG or dPNAG may be conjugated to a carrier (or a carrier compound, as the terms are used interchangeably herein), either directly or via a linker. The conjugation can occur at any position in the polysaccharide, including at one or both of its ends.

A "carrier" as used herein is a compound that can be conjugated to a polysaccharide either directly or through the use of a linker. The carrier may be immunologically active (i.e., immunogenic) or it may be inert. When used in vivo, it should be understood that the carrier is safe for administration to a subject.

Carriers include but are not limited to proteins, or peptides, polysaccharides, nucleic acids, or other polymers, lipids, and small molecules. Carrier proteins include for example, plasma proteins such as serum albumin, immunoglobulins, apolipoproteins and transferrin; bacterial polypeptides such as TRPLE, β-galactosidase, polypeptides such as herpes gD protein, allergens, diphtheria toxoid, tetanus toxoid, *salmonella* flagellin, hemophilus pilin, hemophilus 15 kDa, 28-30 kDa and 40 kDa membrane proteins, *Escherichia coli*, heat label enterotoxin ltb, cholera toxin, and viral proteins including rotavirus VP and respiratory syncytial virus f and g proteins.

Carrier proteins that may be useful for immunization include keyhole limpet hemocyanin, serum albumin, bovine thyroglobulin, or soy bean trypsin inhibitor. Any other compound that is immunogenic in the subject being immunized can be used as a carrier.

Many methods are known in the art for conjugating a polysaccharide to a protein. In general, the polysaccharide should be activated or otherwise rendered amenable to conjugation (i.e., at least one moiety must be rendered capable of covalently bonding to a protein or other molecule). Such methods are known in the art. Reference can be made to published U.S. patent application Nos. US-2005-0118198-A1 and US-2011-0150880-A1 and U.S. Pat. Nos. 4,356,170, 4,663,160, 4,619,828, 4,808,700, 4,711,779.

The carrier may be conjugated to PNAG or dPNAG through a linker or spacer. A polysaccharide may be coupled to a linker or a spacer by any means known in the art including, for example using a free reducing end of the polysaccharide to produce a covalent bond with a spacer or linker. A covalent bond may be produced by converting a free reducing end of PNAG or dPNAG into a free 1-aminoglycocide, that can subsequently be covalently linked to a spacer by acylation. (Lundquist et al., *J. Carbohydrate Chem.*, 10:377 (1991)). Alternatively, PNAG or dPNAG may be covalently linked to the spacer using an N-hydroxysuccinimide active ester as activated group on the spacer. (Kochetkow, *Carbohydrate Research*, 146:C1 (1986)). The free reducing end of PNAG or dPNAG may also be converted to a lactone using iodine and potassium hydroxide. (Isebell et al., *Methods of Carbohydrate Chemistry*, Academic Press, New York (1962)). The lactone can be covalently linked to the spacer by means of a primary amino group on the spacer or linker. The free reducing end of PNAG or dPNAG may also be covalently linked to the linker or spacer using reductive amination.

In some embodiments, the carrier is a tetanus toxoid. A "tetanus toxoid" refers to an inactive form of tetanus toxin. Active tetanus toxin causes the clinical manifestation of tetanus. Examples of tetanus toxoid that can be used in the conjugates of this disclosure are provided for example in Broker et al., Vaccine, 35(25): 3286-3294, 2017, incorporated herein by reference.

In some embodiments, the tetanus toxoid is attached to the polysaccharide via a linker. In some embodiments, the linker has a structure of:

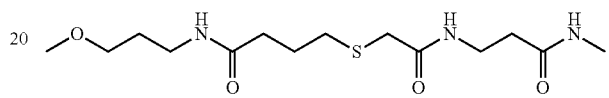

The resulting polysaccharide-carrier conjugate has a structure of:

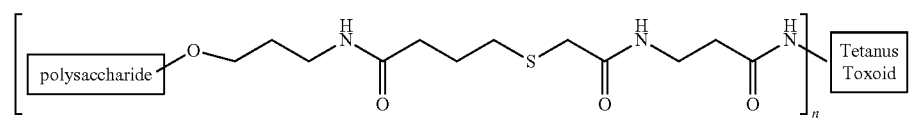

A similar structure is contemplated wherein the polysaccharide is an oligosaccharide. It is to be understood that unless otherwise stated various recitations of polysaccharide, herein, embrace oligosaccharide as well.

Figure 2A:
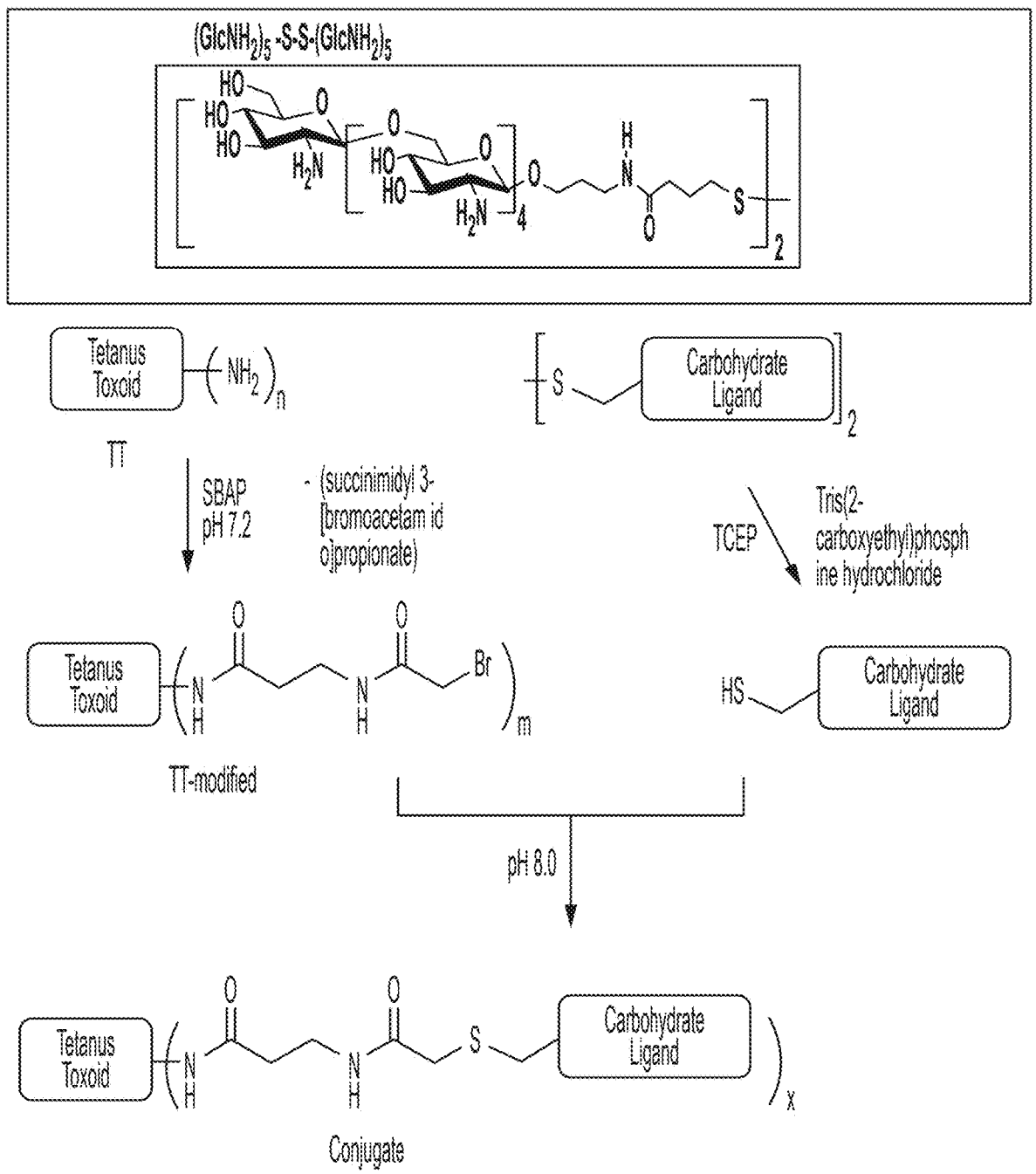
FIGS. 2A-2B are schematics of an exemplary synthetic dPNAG-tetanus toxoid (TT) conjugate vaccine. Tetanus toxoid was used as a carrier for the dPNAG polysaccharide.
Figure 2B:
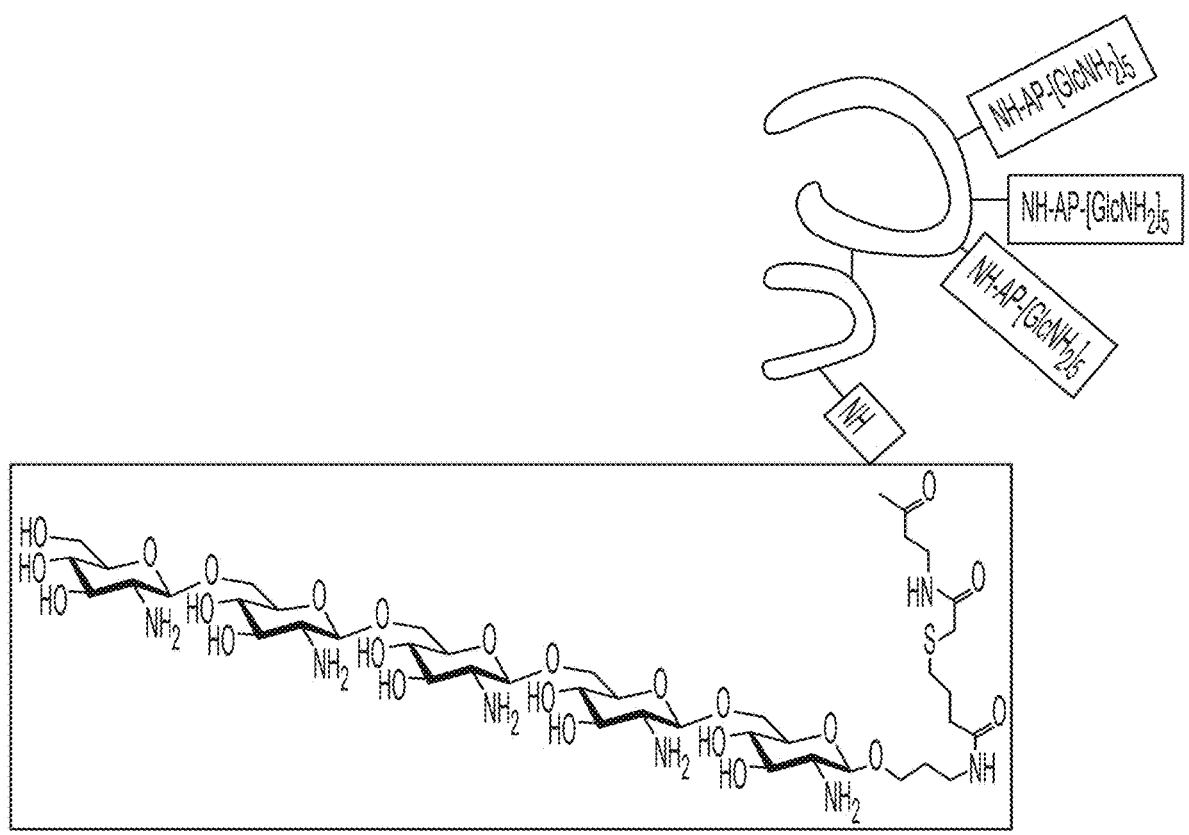

In some embodiments, the polysaccharide-carrier conjugate can be made using the procedure depicted in FIG. 2A.

In some embodiments, one polysaccharide is conjugated to a tetanus toxoid carrier. In some embodiments, a plurality of the polysaccharides are conjugated to the tetanus toxoid carrier. For example, about 1, about 2, about 5, about 10, about 20, about 25, about 30, about 40, about 50, about 60, about 70, about 80, about 90, about 100, about 200, or more polysaccharides may be conjugated to the tetanus toxoid carrier.

Antibodies

The disclosure embraces use of antibodies and antibody fragments that bind to PNAG and/or dPNAG. In some preferred embodiments, the antibodies and antibody fragments bind to epitopes presented by both dPNAG and PNAG, including for example backbone epitopes present in both. The antibodies may be either monoclonal antibodies or polyclonal antibodies. Antibodies may be made using synthetically produced dPNAG, optionally conjugated to a carrier and/or used in conjunction with an adjuvant. Alternatively, antibodies may be produced using dPNAG produced from deacetylation of PNAG. In some instances, antibodies may be produced using PNAG.

As is known in the art, polyclonal antibodies generally are raised in animals by multiple subcutaneous or intraperitoneal injections of an antigen (in conjugated or unconjugated form) and optionally an adjuvant. Polyclonal antibodies to PNAG or dPNAG in conjugated or unconjugated forms can be generated by injecting PNAG or dPNAG in conjugated or unconjugated form, alone or in combination with an adjuvant. Methods for making such polyclonals is described in published U.S. patent application No. US-2005-0118198-A1.

Briefly, dPNAG or PNAG in conjugated or unconjugated form, acting as the antigen, is combined with an adjuvant such as Freund's incomplete adjuvant (e.g., 100 µg of conjugate for rabbits or mice in 1-3 volumes of Freund's) and injected intradermally at multiple sites. Approximately one month later, the animals are boosted with ⅕-⅒ of the original amount of antigen in adjuvant by subcutaneous injection at multiple sites. One to two weeks later the animals are bled, and the serum is assayed for the presence of antibody. The animals may be repeatedly boosted until the antibody titer plateaus. The animal may be boosted with PNAG or dPNAG in conjugated or unconjugated form, with or without an adjuvant. In some embodiments, the boosts may comprise PNAG rather than dPNAG, or dPNAG rather than PNAG, or they may contain a mixture of dPNAG and PNAG.

In addition to supplying a source of polyclonal antibodies, the immunized animals can be used to generate monoclonal antibodies. As used herein, the term "monoclonal antibody" refers to a homogenous (i.e., single clonal) population of immunoglobulins that bind to the same epitope of an antigen. Monoclonal antibodies have the same Ig gene rearrangement and thus demonstrate identical binding specificity. In the case where dPNAG in conjugated or unconjugated form is used to generate the antibodies, the epitope may be present in highly acetylated PNAG as well as dPNAG and thus antibodies raised against dPNAG may also bind to PNAG. This is the case for both polyclonal and monoclonal antibodies.

Methods for preparing monoclonal antibodies are also known in the art. Monoclonal antibodies can be prepared by a variety of methods. In one such method, spleen cells isolated from the immunized animal are immortalized by fusion with myeloma cells or by Epstein Barr Virus transformation, and clones expressing the desired antibody are screened and identified. Other methods involve isolation of rearranged Ig gene sequences and cloning into immortalized cell lines. Such methods are described in greater detail in PCT Application Publication No. WO2005/103084, U.S. Pat. No. 7,786,255 and US Patent Application Publication No. US 20060115486, and such teachings are incorporated by reference herein.

Antibodies specific for PNAG may be, without limitation, murine, human or chimeric antibodies such as but not limited to humanized antibodies.

Human monoclonal antibodies may be made by any of the methods known in the art, including those disclosed in U.S. Pat. Nos. 5,567,610, 5,565,354, 5,571,893, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). Human antibodies may be obtained by recovering antibody-producing lymphocytes from the blood or other tissues of humans producing antibody to an antigen of interest (e.g., dPNAG and/or PNAG). These lymphocytes can be treated to produce cells that grow on their own in the laboratory under appropriate culture conditions. The cell cultures can be screened for production of antibody to the antigen of interest and then cloned. Clonal cultures can be used to produce human monoclonal antibodies to dPNAG and/or PNAG, or the genetic elements encoding the variable portions of the heavy and light chain of the antibody can be cloned and inserted into nucleic acid vectors for production of antibody of different types. In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255-258 (1993), Bruggermann et al., *Year in Immunol.*, 7:33 (1993) and U.S. Pat. No. 5,569,825 issued to Lonberg).

As used herein, a "humanized monoclonal antibody" is a monoclonal antibody or functionally active fragment thereof having at least human constant regions and an antigen-binding region, such as one, two or three CDRs, from a non-human species. Humanized antibodies have particular clinical utility in that they specifically recognize antigens of interest, but will not evoke an immune response in humans against the antibody itself. As an example, murine CDRs may grafted into the framework region of a human antibody to prepare the humanized antibody. See, e.g., L. Riechmann et al., *Nature* 332, 323 (1988); M. S. Neuberger et al., Nature 314, 268 (1985) and EPA 0 239 400. Alternatively, humanized monoclonal antibodies may be constructed by replacing the non-CDR regions of a non-human antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are commercial entities in the United States that will synthesize humanized antibodies from specific murine antibody regions, such as Protein Design Labs (Mountain View Calif.), Abgenix, and Medarex. Reference may also be made to EP Patent Application No. 0239400.

Antigen-binding antibody fragments are also encompassed by the disclosure, and these may be referred to as antibody fragments for brevity throughout this disclosure. As is known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')2 and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)]. Well-known functionally active antibody fragments include but are not limited to F(ab')2, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrilch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the dPNAG epitope. It is to be understood that the epitope recognized by anti-dPNAG antibodies may also be present on highly acetylated PNAG.

In some embodiments, the anti-PNAG antibody is F598 (ATCC PTA-5931) antibody or an antibody fragment thereof. The amino acid sequences of the 6 CDRs and the heavy chain and light chain variable regions are shown below:

F598 heavy chain CDR1:
(SEQ ID NO: 1)
GYYWS

F598 heavy chain CDR2:
(SEQ ID NO: 2)
YIHYSRSTNSNPALKS

F598 heavy chain CDR3:
(SEQ ID NO: 3)
DTYYYDSGDYEDAFDI

F598 light chain CDR1:
(SEQ ID NO: 4)
TLSSGHSNYAIA

F598 light chain CDR2:
(SEQ ID NO: 5)
VNRDGSHIRGD

F598 light chain CDR3:
(SEQ ID NO: 6)
QTWGAGIRV

F598 heavy chain variable region:
(SEQ ID NO: 7)
QVQLQESGPGLVKPSETLSLTCTVSGGSISGYYWSWIRQPPGKGLEWIGY

IHYSRSTNSNPALKSRVTISSDTSKNQLSLRLSSVTAADTAVYYCARDTY

YYDSGDYEDAFDIWGQGTMVTVSS

-continued

F598 light chain variable region:
(SEQ ID NO: 8)
QLVLTQSPSASASLGASVKLTCTLSSGHSNYAIAWHQQQPGKGPRYLMKV

NRDGSHIRGDGIPDRFSGSTSGAERYLTISSLQSEDEADYYCQTWGAGIR

VFGGGTKLTVLG

A further description of antibody F598 is provided in PCT Application Publication No. WO2005/103084, U.S. Patent Application Publication No. US 20060115486 and U.S. Pat. No. 7,786,255, the entire contents of which are incorporated by reference herein.

Other antibodies that may be used in the methods provided herein include F628 and F630, both of which are also described in PCT Application Publication No. WO2005/103084, U.S. Patent Application Publication No. US 20060115486 and U.S. Pat. No. 7,786,255, and those teachings are also incorporated by reference herein.

Uses

PNAG or dPNAG, in conjugated or unconjugated form, and PNAG- and/or dPNAG-specific antibodies of the disclosure are useful in a variety of different applications including in vitro and in vivo applications. PNAG or dPNAG, in conjugated or unconjugated form, may be used to immunize subjects in vivo to prevent or treat infection by filarial parasites and resulting filariasis.

PNAG and more preferably dPNAG may be used to induce an immune response in a subject having or at risk of developing an infection by any PNAG-expressing filarial parasite. Immune response induction may prevent or it may partially or wholly treat the infection. Partial treatment of the infection may include may be observed as partial reduction in pathogen load in the subject. Partial treatment may be useful where a subject is being administered or will be administered one or more other therapeutic agents. Immune response induction is accomplished by administering to the subject an effective amount for inducing an immune response such as an antibody response against PNAG (and thus correspondingly dPNAG) (or pathogens expressing PNAG).

As used herein, a subject is a warm-blooded mammal and includes, for instance, humans, primates, horses, cows, swine, goats, sheep, dogs, and cats. In some embodiments, the subject is a non-rodent subject. A non-rodent subject is any subject as defined above, but specifically excluding rodents such as mice, rats, and rabbits. In some embodiments, the preferred subject is a human. In some embodiments, the subject is a companion animal. In some embodiments, the subject is a canine or feline zoo animal (e.g., a wolf, a lion or a tiger).

The subject may be one having or one at risk of developing an infection by a filarial parasite. A subject at risk of developing an infection by a filarial parasite may be at risk of being exposed to such a pathogen. Populations at risk of developing infection include, for example, human subjects that are likely to travel to locations where filarial parasites or intermediate host carrying filarial parasites are present, and companion animals or zoo animals that have not received any other types of anti-filarial parasite medicament. In some embodiments, the subject has filariasis. In some embodiments, the subject has previously received an anti-filariasis treatment such as an anti-filariasis medicament. Non-limiting examples of anti-filariasis medicaments include diethylcarbamazine (DEC), macrocyclic lactones (e.g., ivermectins, avermectins, and milbemycins), albendazole, and tetracycline, and combinations thereof including diethylcarbamazine and albendazole.

PNAG or dPNAG, in conjugated or unconjugated form, can be administered to the subject in an effective amount for inducing an immune response. Such an effective amount may be an amount sufficient to assist the subject in producing its own immune protection by for example inducing the production of antibodies specific to PNAG and/or dPNAG, inducing the production of memory cells, and possibly a cytotoxic lymphocyte reaction, etc. The immune response may in turn prevent infection by a PNAG-expressing filarial parasites from occurring in a subject that is exposed to such a filarial parasites. One of ordinary skill can assess whether an amount of PNAG or dPNAG, conjugated or unconjugated, is sufficient to induce active immunity by methods known in the art. For instance, the ability of a PNAG or dPNAG, in conjugated or unconjugated form, to produce PNAG-specific antibody in a mammal can be assessed by screening the produced antibodies in a mouse or other subject. In some instances, amounts of PNAG or dPNAG for inducing immune responses may range from about 1 to 100 μg, although they are not so limited.

The antibody or antibody fragment specific for either PNAG or PNAG and dPNAG is useful for inducing passive immunization in a subject, for example, by preventing the development of systemic infection in those subjects at risk of exposure to PNAG-expressing filarial parasites. The method for inducing passive immunity to infection involves administering to a subject an effective amount of an antibody specific for PNAG or of an antibody specific for PNAG and dPNAG for inducing an immune response to PNAG or PNAG-expressing filarial parasites.

The antibody or antibody fragment may be administered to any subject at risk of developing an infection by filarial parasites, and in some embodiments may be particularly suited for subjects incapable of inducing active immunity to PNAG and/or dPNAG. In some subjects, PNAG or dPNAG, in conjugated or unconjugated form, might not be completely effective at preventing or eliminating an infection in certain subjects, and therefore such subjects may benefit from treatment with antibody specific for PNAG or more likely antibody specific PNAG and dPNAG. A subject that is incapable of inducing an active immune response when administered the vaccine includes, but is not limited to, an immunocompromised subject (e.g., a subject undergoing chemotherapy, a subject having AIDS, etc.) or a subject that has not yet developed an immune system (e.g. pre-term neonate).

The antibody or antibody fragment is administered to the subject in an effective amount for inducing an immune response to PNAG or PNAG-expressing filarial parasites. As used herein, an effective amount or antibody or antibody fragment for inducing an immune response is an amount of antibody or antibody fragment that is sufficient to (i) prevent infection from occurring in a subject that is exposed to the filarial parasite; (ii) inhibit the development of infection, i.e., arresting or slowing its development; and/or (iii) relieve the infection, i.e., eradication of the microbe in infected subjects. Pathogen load may be used to observe any one or a combination of these outcomes Using procedures known to those of ordinary skill, one may determine whether an amount of antibody or antibody fragment is effective in an in vitro assay such as that described in the Examples. Filarial parasite infection may be diagnosed by the detection of microfilariae in a direct blood smear, or above the buffy coat in a microhematocrit tube, or using a modified Knott test, or after Millipore filtration. Filarial parasite infection may also be diagnosed by adult antigen testing.

Pharmaceutical Compositions and Formulations

In general, when administered in vivo, the polysaccharides whether conjugated or unconjugated, antibodies and antibody fragments of the disclosure are administered as pharmaceutically acceptable compositions. Such compositions may comprise pharmaceutically acceptable carriers, salts, buffering agents, preservatives, adjuvants, and optionally other prophylactic or therapeutic agents such as those described herein and/or known in the art. A pharmaceutically-acceptable carrier means one or more compatible solid or liquid filler, diluents or encapsulating substances which are suitable for administration to a human or other animal. In the context of a pharmaceutically acceptable carrier, the term "carrier" denotes an organic or inorganic ingredient, natural or synthetic, with which the polysaccharide, antibody or antibody fragment is combined to facilitate use including administration. The components of the pharmaceutical compositions should also be capable of being commingled with the polysaccharide, antibody or antibody fragment, and with each other, in a manner such that there is no interaction which would substantially impair the desired pharmaceutical efficiency.

Pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

Compositions suitable for parenteral administration typically comprise a sterile aqueous preparation of the polysaccharide, antibody or antibody fragment, which may be isotonic with the blood of the recipient subject. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The polysaccharides, antibodies and antibody fragments are administered in effective amounts. Polysaccharide or oligosaccharide doses ranging from 1-100 μg may be effective, depending on the mode of administration and the particular intended result. Antibody or antibody fragment doses ranging from 0.1-100 mg/kg and 0.1-20 mg/kg, depending upon the mode of administration, may be effective. The absolute amount will depend upon a variety of factors including whether the administration is performed on a high risk subject not yet infected or on a subject already having an infection, the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the polysaccharides, antibodies and/or antibody fragments are contemplated. Generally immunization schemes involve the administration of a first dose, which may be a high dose, of an antigen followed by subsequent doses, which may be lower doses, of antigen after a waiting period of several weeks. Further doses may be administered as well. The dosage schedule for passive immunization would be quite different with more frequent administration if necessary. Any regimen that results in an enhanced immune response to infection and/or subsequent protection from infection may be used. Desired time intervals for delivery of multiple doses of a particular antigen can be determined by one of ordinary skill in the art employing no more than routine experimentation. Vaccine doses may be administered over a period of 1 to 6 months, optionally with doses equally spaced apart in time. For antibodies and antibody fragments, dosing intervals generally range from 14-180 days.

A variety of administration routes are available. The particular mode selected will depend upon, for example, the particular condition being treated and the dosage required for therapeutic efficacy. The methods of this disclosure, generally speaking, may be practiced using any mode of administration that is medically acceptable, meaning any mode that produces effective levels of an immune response without causing clinically unacceptable adverse effects. In some embodiments, the administration is via systemic routes. In some embodiments, the administration is via parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

Other delivery systems can include time-release, delayed release or sustained release delivery systems. Such systems can avoid repeated administrations of the polysaccharides of the disclosure, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and 3,854,480 (Zaffaroni). In addition, a pump-based hardware delivery system can be used, some of which are adapted for implantation.

Secondary Agents

PNAG and dPNAG, whether conjugated or unconjugated, and/or PNAG-specific antibodies or antibodies that bind PNAG and dPNAG may be delivered in conjunction with other agents. The nature of the other agent(s) may depend upon whether the antigen (e.g., dPNAG conjugate) or antibody (e.g., antibody that binds to dPNAG and PNAG) is being administered.

For example, when administered to induce active immunity and/or to produce antibody, dPNAG may be used in conjunction with an adjuvant. As used herein, the term adjuvant refers to a substance that is administered in conjunction with (including at the same time, in the same formulation, etc.) an antigen (such as dPNAG) in order to potentiate an antigen-specific immune response. Adjuvants include but are not limited to aluminum compounds, e.g., gels, aluminum hydroxide and aluminum phosphate, and Freund's complete or incomplete adjuvant (e.g., in which the dPNAG antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide. Rare earth salts, e.g., lanthanum and cerium, may also be used as adjuvants. The amount of adjuvant depends on the subject and the particular antigen used and can be determined by one skilled in the art without undue experimentation. One example of an adjuvant suitable for use in dogs is Montanide PetGelA.

Polysaccharide antigens (other than PNAG and dPNAG) and polysaccharide-specific antibodies (other than PNAG-specific antibodies) are known in the art. Examples include *Salmonella typhi* capsule Vi antigen (Szu, S. C., X. Li, A. L. Stone and J. B. Robbins, Relation between structure and immunologic properties of the Vi capsular polysaccharide, *Infection and Immunity*. 59:4555-4561 (1991)); *E. Coli* K5 capsule (Vann, W., M. A. Schmidt, B. Jann and K. Jann, The structure of the capsular polysaccharide (K5 antigen) of urinary tract infective *Escherichia coli*, 010:K5:H4. A polymer similar to desulfo-heparin, *European Journal of Biochemistry*. 116: 359-364, (1981)); *Staphylococcus aureus* type 5 capsule (Fournier, J.-M., K. Hannon, M. Moreau, W. W. Karakawa and W. F. Vann, Isolation of type 5 capsular polysaccharide from *Staphylococcus aureus*, *Ann. Inst. Pasteur/Microbiol*. (Paris). 138: 561-567, (1987)); *Rhizobium melilori* expolysaccharide II (Glazebrook, J. and G. C. Walker, a novel expolysaccharide can function in place of the calcofluor-binding exopolysaccharide in nodulation of alfalfa by *Rhizobium meliloti*, *Cell*. 65:661-672 (1989)); Group B *Streptococcus* type III (Wessels, M. R., V. Pozsgay, D. L. Kasper and H. J. Jennings, Structure and immunochemistry of an oligosaccharide repeating unit of the capsular polysaccharide of type III Group B *Streptococcus*, *Journal of Biological Chemistry*. 262:8262-8267 (1987)); *Pseudomonas aeruginosa* Fisher 7 O-specific side-chain (Knirel, Y. A., N. A. Paramonov, E. V. Vinogradov, A. S. Shashkow, B. A. N. K. Kochetkov, E. S. Stanislaysky and E. V. Kholodkova, Somatic antigens of *Pseudomonas aeruginosa* The structure of 0-specific polysaccharide chains of lipopolysaccharides of *P. aeruginosa* O3 (Lanyi), 025 (Wokatsch) and Fisher immunotypes 3 and 7, *European Journal of Biochemistry*. 167:549, (1987)); *Shigella sonnei* O-specific side chain (Kenne, L., B. Lindberg and K. Petersson, Structural studies of the O-specific side-chains of the *Shigella sonnei* phase I lipopolysaccharide, *Carbohydrate Research*. 78:119-126, (1980)); *S. pneumoniae* type I capsule (Lindberg, B., Lindqvist, B., Lonngren, J., Powell, D. A., Structural studies of the capsular polysaccharide from *S.*

*pneumoniae* type 1, Carbohydrate Research. 78:111-117 (1980)); and *S. pneumoniae* group antigen (Jennings, H. J., C. Lugowski and N. M. Young, Structure of the complex polysaccharide C-substance from *S. pneumoniae* type 1, Biochemistry. 19:4712-4719 (1980)). Other non-polysaccharide antigens and non-polysaccharide specific antibodies are known to the those of skill in the art and can be used in conjunction with the compositions of the disclosure.

In some embodiments, PNAG, dPNAG, polysaccharide-carrier conjugate vaccines and/or PNAG-specific antibodies may be administered with anti-filarial agents (also referred to herein as anti-filarial medicaments). Anti-filarial agents include but are not limited to diethylcarbamazine (DEC), macrocyclic lactones (e.g., ivermectins, avermectins, abamectins, and milbemycins), moxidectin and tetracycline. Still other anti-filarial agents include levamisole, amodiaquine, albendazole, doxycycline, melaminylthioarsenate (also known as melarsomine, Immiticide, and Diroban), and arsenamide (also known as thiacetarsamide and Caparsolate). The anti-filarial agents may also be used in combination such as for example albendazole and DEC or albendazole and ivermectin. The macrocyclic lactones are typically used for prevention of filariasis, such as heartworm infection in dogs. Treatment of existing infection, such as heartworm infection in dogs, may use melarsomine.

In some instances, use of the antigen (e.g., dPNAG conjugated to a protein carrier such as tetanus toxoid) or antibody (e.g., antibody that binds to dPNAG and PNAG) or antibody fragments thereof may shorten the number of treatments and/or time course of treatment using anti-filarial agents. For example, if the standard of care is to administer an anti-filarial agent for each of 12 days, then when such agent is used in conjunction with the antigens and/or antibodies or antibody fragments provided herein the 12 day regimen may be reduced for example by 25%, 50%, 75%, 80%, 90% or more. Alternatively, the regimen may be altered such that the anti-filarial agent is administered 1 day, 2 days, 3 days, 4 days, 5 days, 6 days, 7 days, 8 days, 9 days, 10 days, or 11 days less than the prior standard of care. Alternatively or additionally, the frequency of administration of the anti-filarial agent may be reduced such that the agent is administered every other day, every third day, every fourth day, every fifth day, every sixth day, every week, every 2 weeks, every 3 weeks, every 4 weeks, every month, every 6 weeks, every 2 months, etc. In still other embodiments, the dose of the anti-filarial agent may be reduced without loss of therapeutic efficacy. The dose may be reduced by at least 1%, 5%, 10%, 15%, 20%, 25%, 30%, 35%, 40%, 45%, 50%, or more. Reduction in the dose administered, and/or the number and frequency of administrations, may help to reduce side effects associated with the anti-filarial such as dizziness, nausea, fever, headache, and/or muscle or joint pain.

In still other embodiments, the antigens or antibodies or antibody fragments may be used when the underlying infection is or has become resistant to the anti-filarial agent(s).

In some embodiments, the antigens or antibodies or antibody fragments may be administered with one or more components of the complement system. A complement system is an enzyme cascade that is a collection of blood and cell surface proteins that help antibodies to clear pathogens from the recipient. The complement system comprises 30 different proteins, including serum proteins, serosal proteins, and cell membrane receptors. There are three different complement pathways, the classical complement pathway, the alternative complement pathway, and the mannose-binding lectin pathway. Components of the complement systems are commercially available, e.g., from Sino Biological.

The following Examples are included for purposes of illustration and are not intended to limit the scope of the disclosure.

EXAMPLES

Example 1: Detection of PNAG on L1, L3, and Adult Stages of *Dirofilaria immitis* and L1 Stage *Acanthocheilonema viteae*

Figure 3:
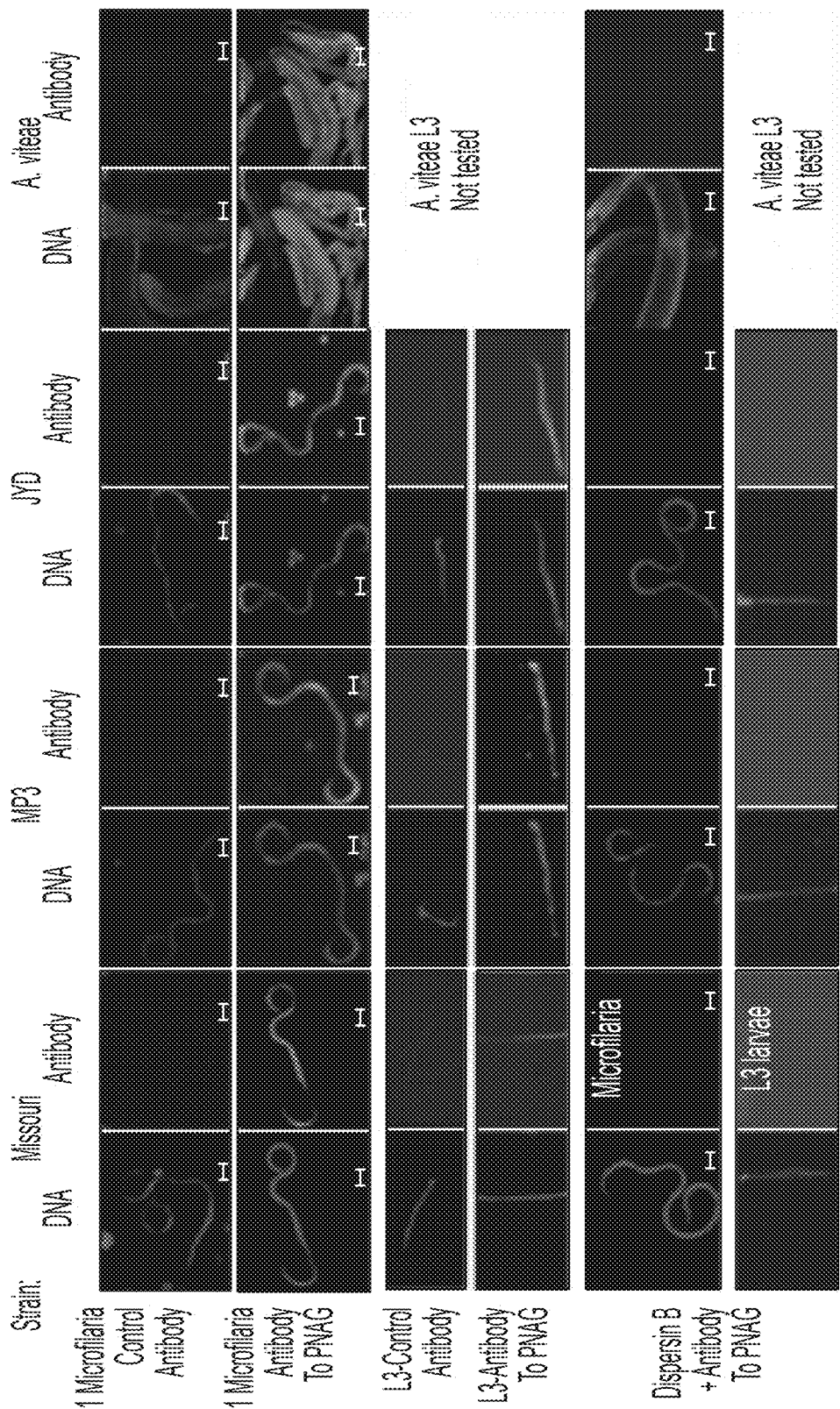
FIG. 3 shows immunostaining images demonstrating the detection of PNAG on L1 and L3 stages of three *Dirofilaria immitis* strains and on L1 stage *A. vitae*. Color versions of the Figure are available upon request.

Three strains of *Dirofilaria immitis* (Missouri, MP3, and YJD) and an *Acanthocheilonema viteae* strain were tested. Parasites were detected by staining for their DNA (shown in red). PNAG antibody (MAb F598) was used to detect PNAG expression (shown in green). MAb F598 binds readily to both microfilarial (L1 stage) and L3 stages of *Dirofilaria immitis* (FIG. 3). Treatment of the parasites with the PNAG-degrading enzyme Dispersin B abolishes reactivity of the anti-PNAG MAb (FIG. 3). Control MAb to *P. aeruginosa* alginate fails to bind to any form of *Dirofilaria immitis*. PNAG was also detected on L1 stage *Acanthocheilonema viteae* (FIG. 3). L3 stage *Acanthocheilonema viteae* was not tested. White bars for microfilaria=10 μm.

Figure 4A:
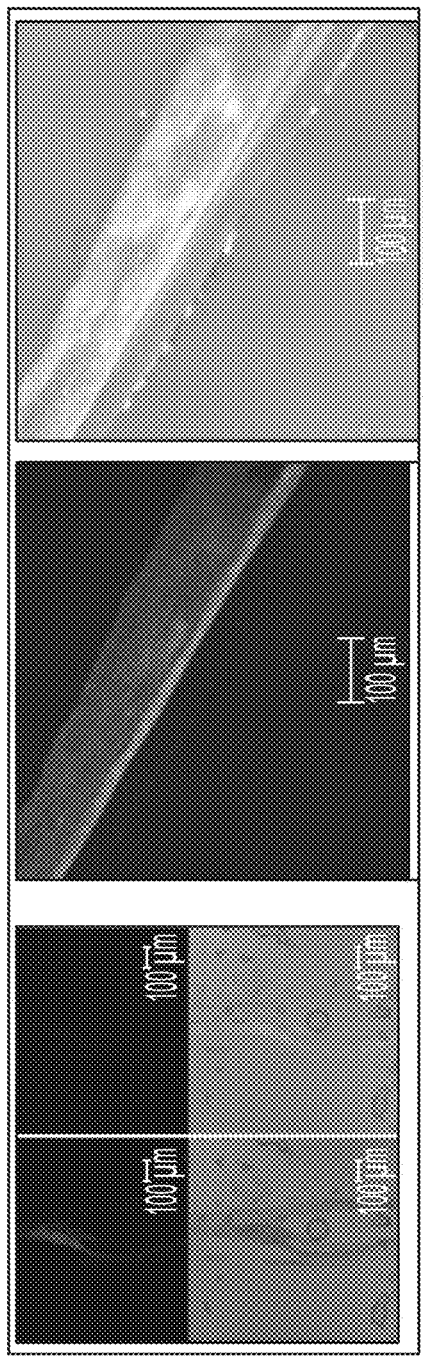
FIGS. 4A-4B show immunostaining images demonstrating the detection of PNAG on adult *Dirofilaria immitis*.
Figure 4B:
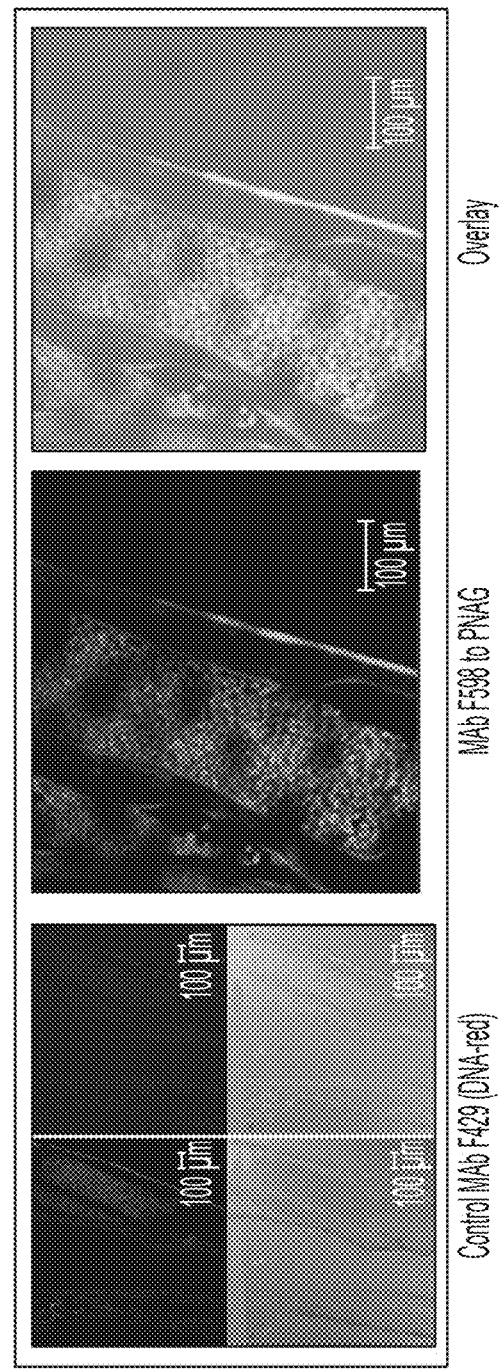

PNAG was also detected on male and female adult *Dirofilaria immitis*. Chitinase treated *Dirofilaria immitis* strain 012315 (male) and strain 2015006 (female) were tested for PNAG expression. PNAG MAb F598 was used for the detection (green). *Dirofilaria immitis* DNA was shown in red. PNAG was detected on the surface of both male (FIG. 4A) and female (FIG. 4B) *Dirofilaria immitis*. There appears to be PNAG expression on female *Dirofilaria immitis* internal structures as well (FIG. 4B).

Figure 5:
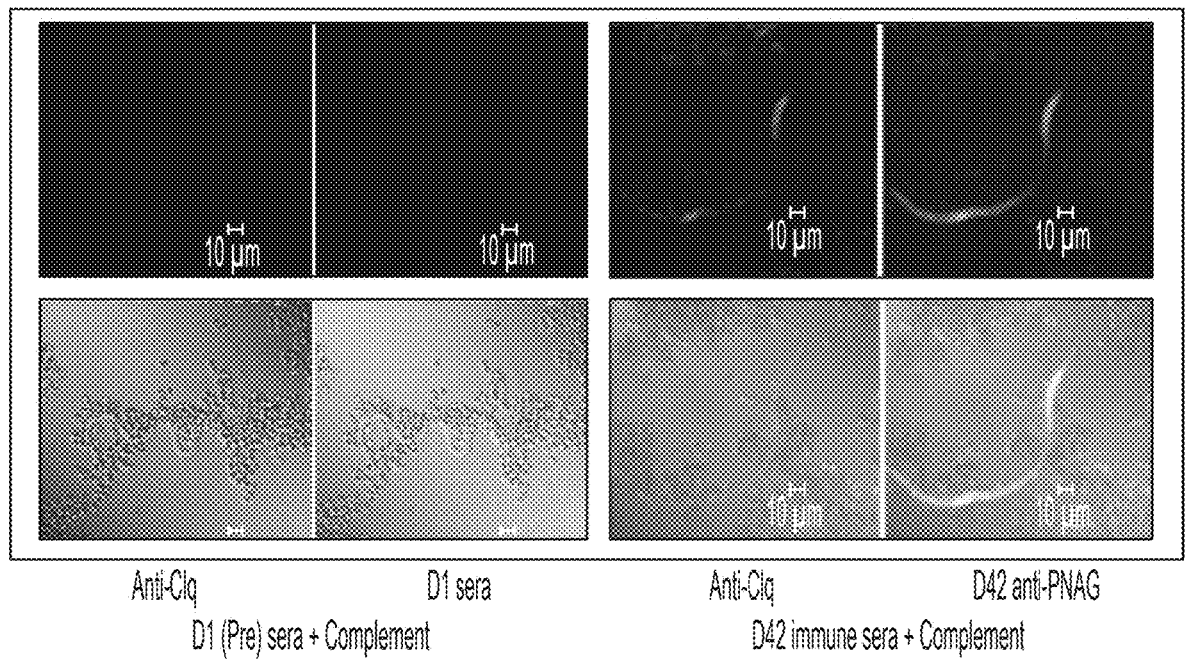
FIG. 5 shows immunostaining images demonstrating the deposition of dog C1q onto L1 stage of *Dirofilaria immitis* drug resistant strain JYD. Lower panels: phase contrast and overlap of C1q and anti-PNAG binding. Bar=10 μm. Color versions of the Figure are available upon request.
Figure 6:
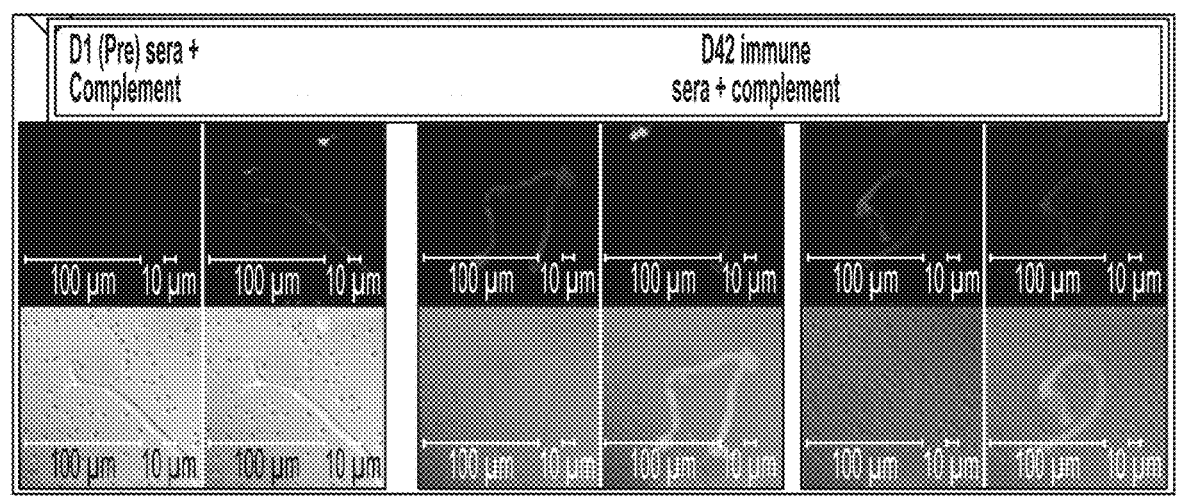
FIG. 6 shows immunostaining images demonstrating that antibody specific to PNAG killed L1 stage *Dirofilaria immitis* drug resistant strain JYD. Short bar=10 μm; long bar=100 μm. Color versions of the Figure are available upon request.

Example 2: Deposition of Dog C1q onto L1 Stage of *Dirofilaria immitis* Drug Resistant Strain JYD Blood of dog infected with *Dirofilaria immitis* drug-resistant strain JYD was obtained. Sera from dogs on day 1 (pre-immunization) or day 42 post-immunization with dPNAG were obtained and added to the infected dog blood. The binding of either dog C1q (red) or dog IgG (green) onto the worm surface was detected 90 minutes later and the results showed that the day 42 anti-PNAG immune sera binds to the L1 surface and deposits complement (FIG. 5).

Example 3: Antibody to PNAG Kills L1 and L3 Stage of *Dirofilaria immitis* Drug Resistant Strain JYD Blood of dog infected with *Dirofilaria immitis* drug-resistant strain JYD was obtained. Sera from dogs on day 1 (pre-immunization) or day 42 post-immunization with dPNAG were obtained and added to the infected dog blood. The results showed that the day 42 anti-PNAG immune sera were able to kill L1 *Dirofilaria immitis* (FIG. 6) with complement. The percentage of live and dead L1 stage *Dirofilaria immitis* were shown in Table 1. In Table 1, indicated component of dog serum was used as a complement source. 10% pre- or post PNAG immune sera were added to dog blood carrying L1 stages of *Dirofilaria immitis* microfilaria. After 48 hours, L1 microfilaria were determined to be live or dead. Cell impermeant propidium iodide was used to detect dead (and non-motile) microfilaria. Syto 15 was used to detect live L1 microfilaria.

TABLE 1

Percentage of live and dead L1 stage *Dirofilaria immitis* after PNAG specific antibody killing

| Tube # | Sample Contents | Live | Dead | % Live | % Dead |
|---|---|---|---|---|---|
| 1 | No Complement & No Antibody | 5 | 1 | 83% | 17% |
| 2 | 10% Complement & No Antibody | 6 | 0 | 100% | 0% |
| 3 | 10% Complement & Pre-Immune Male Dog Antiserum | 5 | 1 | 83% | 17% |
| 4 | 10% Complement & Pre-Immune Female Dog Antiserum | 6 | 0 | 100% | 0% |
| 5 | 10% Complement & PNAG-Immune Male Dog Antiserum | 2 | 4 | 33% | 67% |
| 6 | 10% Complement & PNAG-Immune Female Dog Antiserum | 1 | 5 | 17% | 83% |
|  | Sum-Control Samples | 22 | 2 | 91.70% | 9.30% |
|  | Sum-Anti-PNAG Immune Sera | 3 | 9 | 25% | 75% |
|  |  |  |  |  | $p = 0.0001$ Fisher's Exact Test |

Figure 7:
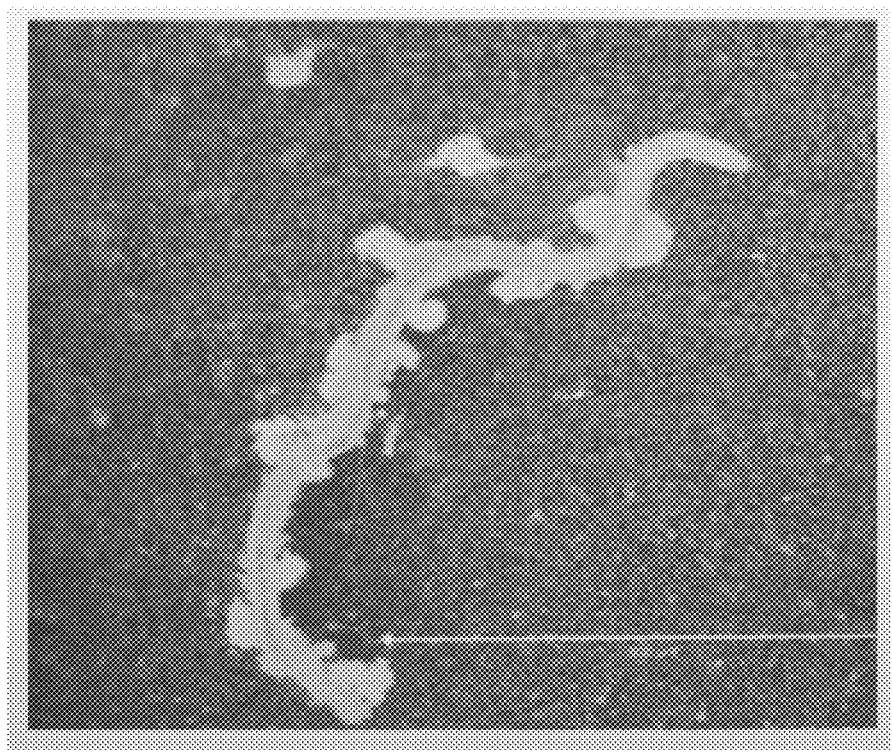
FIG. 7 shows that in the presence of PNAG-immune dog antiserum, canine polymorphonuclear leukocytes (PMNs) adhered to *Dirofilaria immitis* L3 larvae and initiated the killing process.

Further, in the presence of anti-PNAG immune dog sera, canine polymorphonuclear leukocytes (PMNs) adhered to *Dirofilaria immitis* L3 larvae and initiated the killing process (FIG. 7).

Figure 8:
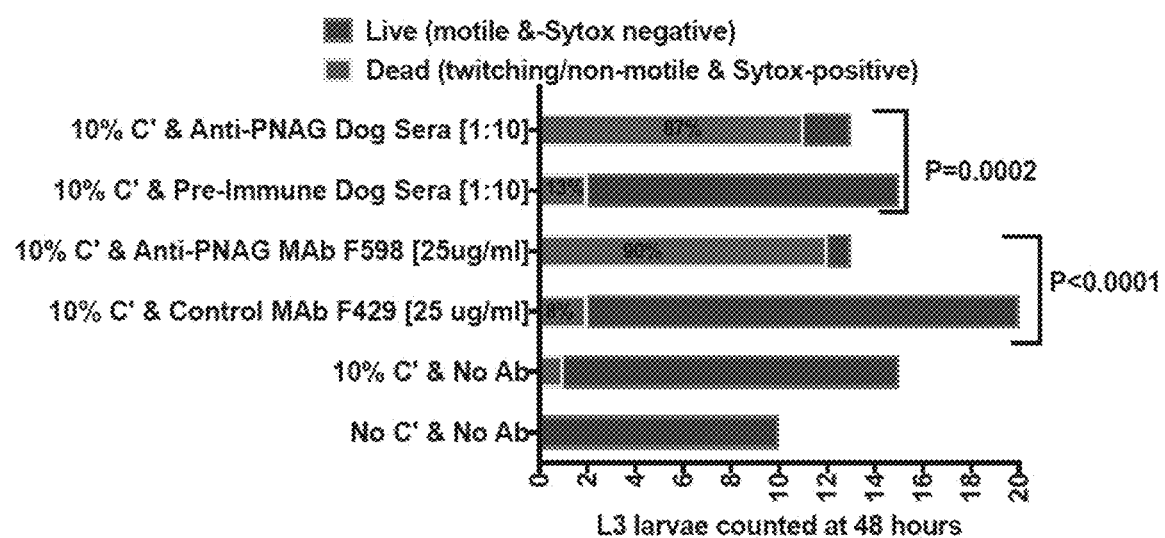
FIG. 8 is a graph showing that polyclonal canine antibodies or monoclonal human antibody to PNAG plus complement killed L3 stage *Dirofilaria immitis* drug resistant strain JYD when added to infected dog blood. C'=complement; MAb F598=Human IgG1 monoclonal antibody to PNAG; MAb F429=control human IgG1 MAb to irrelevant antigen. The numbers in the bars represent the % of dead L3 larvae. The first portion of each bar represents the dead larvae. In the no C' and no Ab control (last bar), all the larvae are alive.

Polyclonal canine antibodies or monoclonal human antibody to PNAG plus complement killed L3 stage of *Dirofilaria immitis* drug resistant strain JYD when added to infected dog blood (FIG. 8). Interestingly, antiserum from female dogs was more effective than antiserum from male dogs, as shown in Table 1 (compare 5 and 6).

Figure 9:
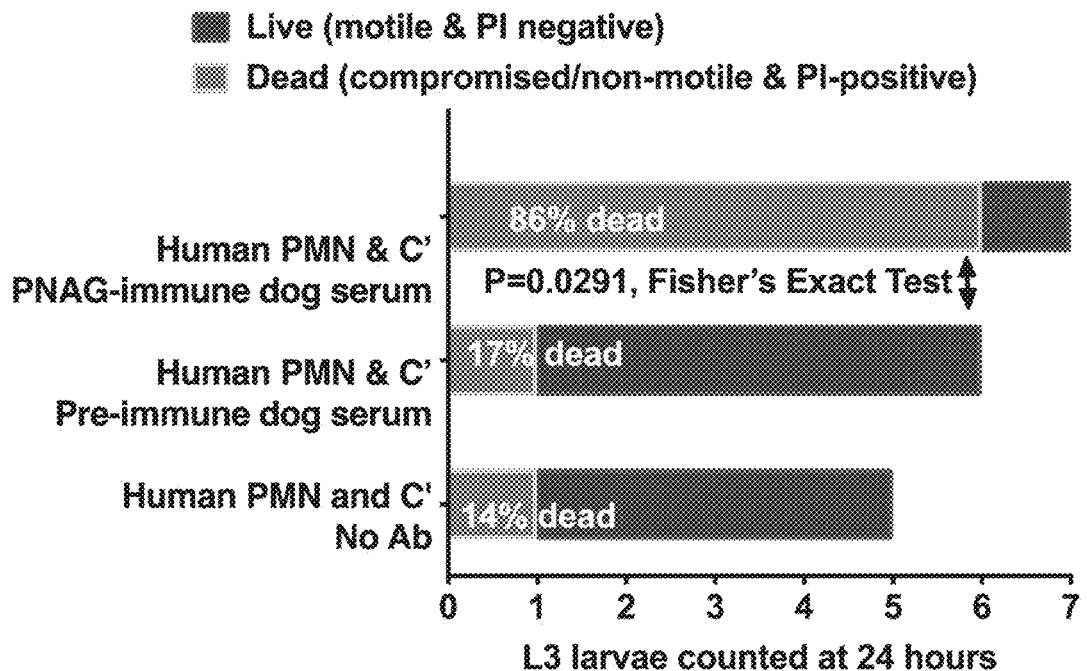
FIG. 9 is a graph showing that antibodies to PNAG plus complement killed L3 stage *Dirofilaria immitis* drug resistant strain JYD when added to human polymorphonuclear neutrophils (PMN) and 10% human complement (C'). The numbers in the bars represent the % of dead L3 larvae. The first portion of each bar represents the dead larvae. Thus, the % dead larvae from top to bottom are 86%, 17% and 14%.

In another set of experiments, dogs were administered the 5-mer conjugate vaccine (as given to humans in FIG. 11) in two doses of 100 micrograms each in the adjuvant Montanide PetGelA, on days 1 and 22. Serum was obtained from the dogs on day 43. Pre-immune serum (obtained on day 1 prior to administration of the vaccine) and post-immune serum (obtained on day 43) from 5 dogs were pooled, and then added to human PMN and human complement and the L3 stage JYD. The results showed that polyclonal canine antibodies to PNAG mediate killing of L3 stage of *D. immitis* drug resistant strain JYD in the presence of human complement and human PMN (phagocytes) (FIG. 9).

In summary, *D. immitis* L1, L3 and L5 surfaces are positive for PNAG. Human monoclonal antibody and canine polyclonal sera to PNAG deposit canine C1q onto the surface of L1 and L3 stages. Antibody to PNAG plus complement mediates killing of L1 and L3 stages of *D. immitis*.

Example 4: Detection of PNAG on L3 Stage of *Brugia malayi* and PNAG-Specific Killing

Figure 10:
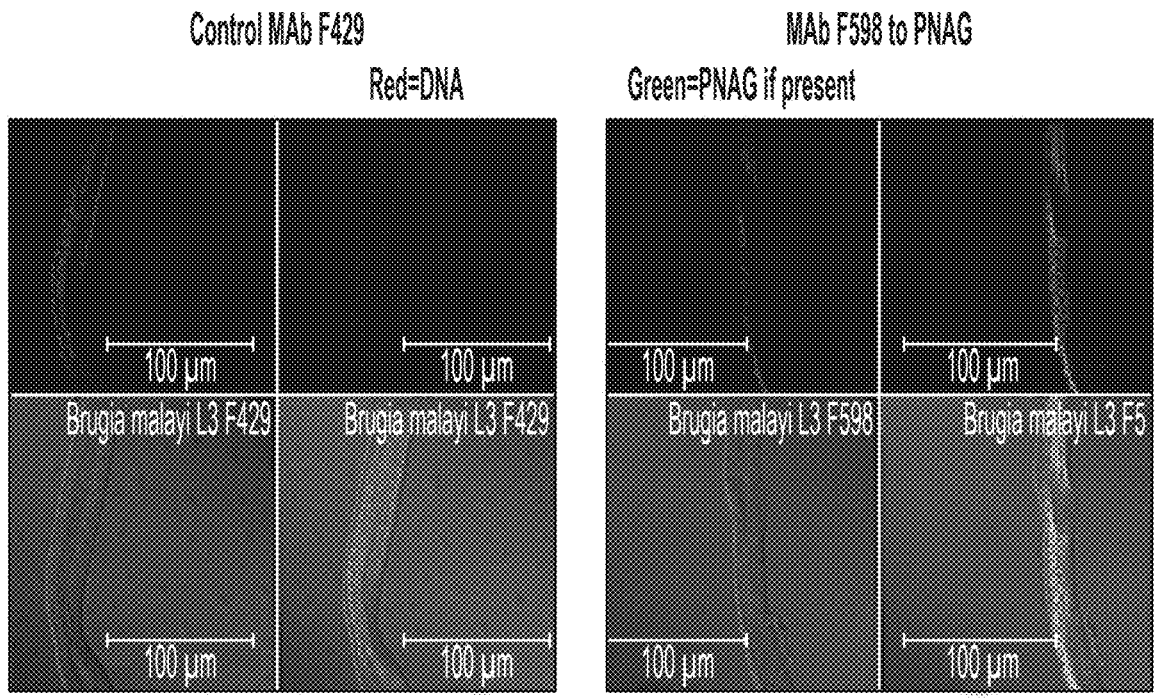
FIG. 10 shows immunostaining images demonstrating the detection of PNAG on L3 stages of *Brugia malayi*, the causative agent of human lymphatic filariasis. MAb=monoclonal antibody. In each panel the upper left shows DNA stain, the upper right detects the presence of PNAG, the lower left is a phase contrast micrograph and the lower right is the overlay of the red and green channels. Color versions of the Figure are available upon request.

*Brugia malayi* is the causative agent of human lymphatic filariasis. FIG. 10 provides immunostaining images demonstrating the detection of PNAG on L3 stages of *Brugia malayi*. In the right panel, the upper left quadrant shows DNA stain (shown in red), the upper right quadrant detects the presence of PNAG (using the F598 anti-PNAG MAb) (shown in green), the lower left quadrant is a phase contrast micrograph, and the lower right quadrant is the overlay of the red and green channels. The left panel uses the control antibody to an irrelevant antibody to rule out non-specific antibody binding. The quadrants are the same as in the right panel except that the upper right quadrant detects the presence of binding to the control MAb. No green signal is apparent.

Figure 11:
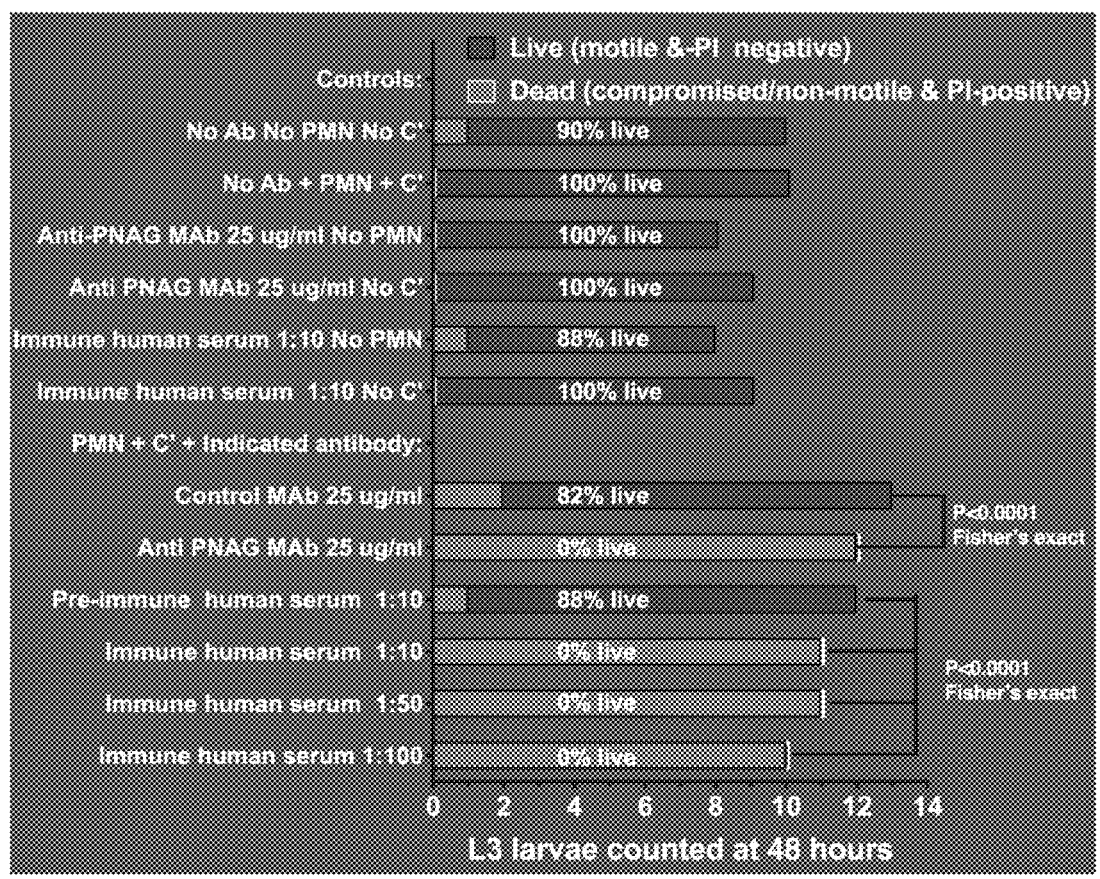
FIG. 11 is a bar graph that shows that human monoclonal and polyclonal antibody to PNAG plus PMN plus complement kills L3 stage of *B. malayi*, the causative agent of the human disease lymphatic filariasis. Ab=antibody; C'=complement; MAb=monoclonal antibody. Pre-immune and immune human serum from individual vaccinated twice, 28 days apart with the 5GlcNH$_2$-TT conjugate vaccine. Pre-immune serum obtained on day of vaccination, post-immune serum obtained 4 weeks after the second dose. The numbers in the bars represent the % of live L3 larvae. The first portion of each bar represents the dead larvae.

Human monoclonal and polyclonal antibody to PNAG kills the L3 stage of *B. malayi* in the presence of human PMN and human complement (FIG. 11). Pre-immune and immune human serum were obtained from an individual vaccinated twice, 28 days apart, with the 5GlcNH2-TT conjugate vaccine. Pre-immune serum was obtained on day 1 of vaccination, post-immune serum was obtained 4 weeks after the second dose. No or low levels of killing were observed in the absence of antibody, PMN and/or complement. Control antibody (MAb F429) in the presence of human PMN and complement killed about 18% of *B. malayi* L3 larvae, in contrast to anti-PNAG MAb which killed 100% of *B. malayi* L3 larvae under the same conditions. Pre-immune human serum in the presence of human PMN and human complement killed about 12% of *B. malayi* L3 larvae, while human anti-serum obtained at day 43 killed 100% of *B. malayi* L3 larvae at dilutions of 1:10, 1:50 and 1:100.

EQUIVALENTS

The foregoing written specification is considered to be sufficient to enable one skilled in the art to practice the disclosure. The present disclosure is not to be limited in scope by examples provided, since the examples are intended as a single illustration of one aspect of the disclosure and other functionally equivalent embodiments are within the scope of the disclosure. Various modifications of the disclosure in addition to those shown and described herein will become apparent to those skilled in the art from the foregoing description and fall within the scope of the appended claims. The advantages and objects of the disclosure are not necessarily encompassed by each embodiment of the disclosure.

All references, patents and patent publications that are recited in this application are incorporated by reference herein in their entirety, unless otherwise indicated.

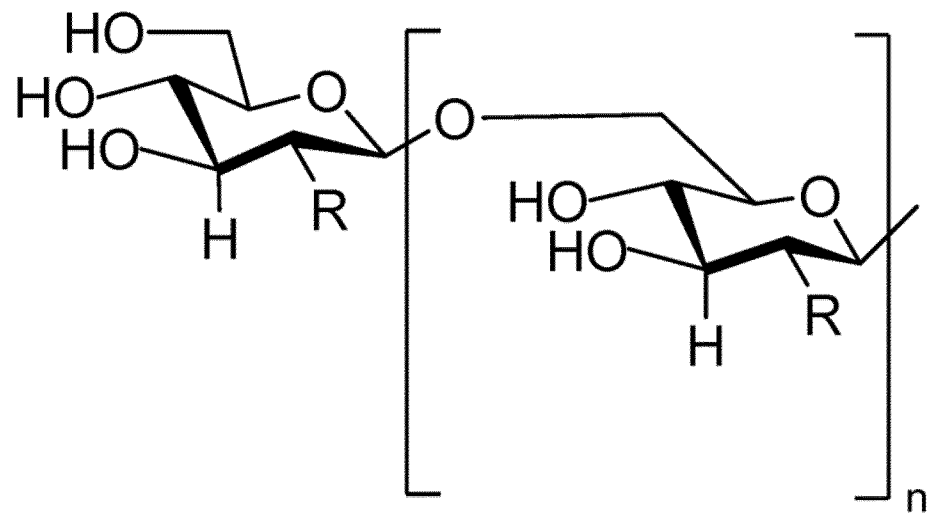

What is claimed is:

1. A method for treating a subject having filariasis, comprising
administering to a subject having filariasis a deacetylated poly-N-acetyl glucosamine (dPNAG) conjugated to a carrier compound in an effective amount to treat filariasis in the subject,
wherein the dPNAG has a structure

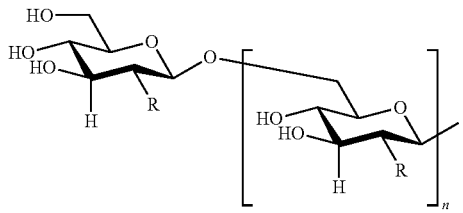

wherein n is at least 4, R is selected from the group consisting of —NH—CO—CH$_3$ and —NH$_2$, provided that less than 50% of the R groups are —NH—CO—CH$_3$.

2. The method of claim 1, wherein the dPNAG is conjugated to the carrier compound through a linker.

3. The method of claim 1, wherein the carrier compound is a peptide or protein carrier.

4. The method of claim 3, wherein the peptide or protein carrier is tetanus toxoid.

5. The method of claim 1, wherein less than 30%, less than 20%, less than 10%, or less than 5% of R groups are —NH—CO—CH$_3$.

6. The method of claim 1, wherein the R group is —NH$_2$.

7. The method of claim 1, wherein n is 4.

8. The method of claim 1, wherein n is 5, 6, 7, or 8.

9. The method of claim 1, wherein a plurality of the dPNAG are conjugated to the carrier compound, and wherein the carrier compound is a peptide or protein carrier.

10. The method of claim 1, wherein the subject is a dog or a cat.

11. The method of claim 10, wherein the filariasis is caused by *Dirofilaria immitis, Acanthocheilonema* spp., or *Brugia* spp.

12. The method of claim 10, wherein the filariasis is caused by *Dirofilaria immitis* that is resistant to an anti-filariasis medicament.

13. The method of claim 10, wherein the filariasis is caused by *Dirofilaria immitis* that is resistant to ivermectin, avermectin, and/or milbemycin.

14. The method of claim 1, wherein the dPNAG is administered with an adjuvant.

15. A method for treating a subject having filariasis, comprising administering to a subject having filariasis an effective amount of an antibody or antibody fragment that binds to poly-N-acetyl glucosamine (PNAG) and deacetylated PNAG (dPNAG).

* * * * *

UNITED STATES PATENT AND TRADEMARK OFFICE
CERTIFICATE OF CORRECTION

| | | |
|---|---|---|
| PATENT NO. | : 12,397,014 B2 | Page 1 of 2 |
| APPLICATION NO. | : 17/427763 | |
| DATED | : August 26, 2025 | |
| INVENTOR(S) | : Gerald B. Pier et al. | |

It is certified that error appears in the above-identified patent and that said Letters Patent is hereby corrected as shown below:

In the Claims

In Claim 1, at Column 33, Line 10, please delete:

"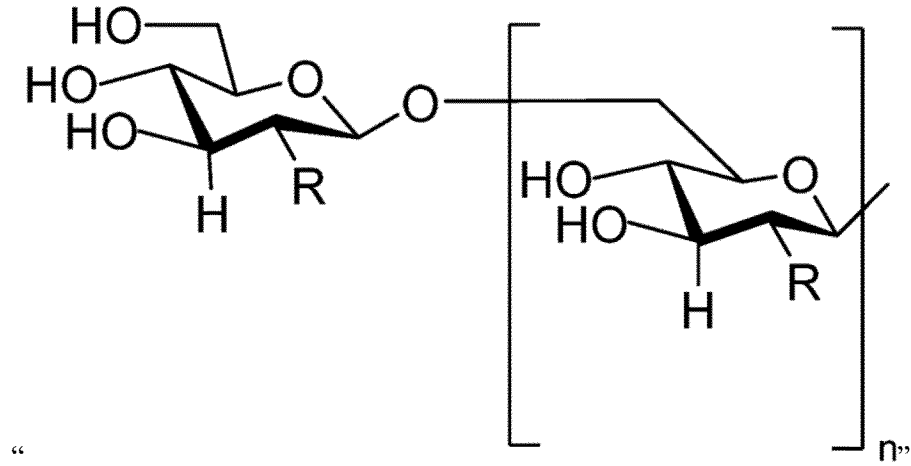"

Signed and Sealed this
Tenth Day of February, 2026

John A. Squires
*Director of the United States Patent and Trademark Office*

CERTIFICATE OF CORRECTION (continued)
U.S. Pat. No. 12,397,014 B2

And replace with: